(12) United States Patent
Turley

(10) Patent No.: US 6,271,344 B1
(45) Date of Patent: Aug. 7, 2001

(54) ENHANCED AFFINITY HYALURONAN BINDING PEPTIDES

(75) Inventor: Eva A. Turley, Toronto (CA)

(73) Assignee: Cangene Corporation, Winnipeg (CA)

(*) Notice: Subject to any disclaimer, the term of this patent is extended or adjusted under 35 U.S.C. 154(b) by 0 days.

(21) Appl. No.: 09/210,896

(22) Filed: Dec. 16, 1998

Related U.S. Application Data

(60) Provisional application No. 60/068,285, filed on Dec. 19, 1997.

(51) Int. Cl.[7] .................. A61K 38/00; A61K 38/04; C07H 5/04; C07H 5/06
(52) U.S. Cl. .................. 530/326; 536/55.2; 514/14
(58) Field of Search .................. 530/326; 536/55.2; 514/14

(56) References Cited

FOREIGN PATENT DOCUMENTS

WO 93/21312   10/1993   (WO).
WO 97/42111   7/1997    (WO).

OTHER PUBLICATIONS

Aruffo, A. et al., *Cell* 61: 1303–1313, 1990.
Boudreau, N. et al., *Dev. Biol.* 143: 235–247, 1991.
Dillon, P.W. et al., *J. Surg. Res.* 57: 170–173, 1994.
Entwistle, J. et al., *Gene* 163: 233–238, 1995.
Entwistle, J. et al., *J. Cell Biol.* 61:569–577, 1996.
Goa, K.L. and Benfield, P., *Drugs* 47: 536, 1994.
Gunthert, U. et al., *Cell* 65: 13–24, 1991.
Hall, C.L. et al., *Cell* 82: 1–20, 1995.
Hall, C.L. & Turley, E.A., *J. Neuro–oncol.* 26: 221–229, 1995.
Hall, C.L. et al., *J. Cell. Biol.* 126:575–588., 1994.
Hardwick, C. et al., *J. Cell. Biol.* 117: 1343–1350, 1992.
King, S.R. et al., *Surgery* 109: 76–84, 1991.
Knudson W., *Ciba Found. Symp.* 143: 150–169, 1989.
Laurent, T.C. and Fraser, J.R.E., *FASEB J.* 6: 2397–2404, 1992.
Lesley, J. et al., *Exp. Cell Res.* 187: 224–233, 1990.
Masellis–Smith, A. et al., *Blood* 87: 1891–1899, 1996.
McCourt, P.A.G. et al., *J. Biol. Chem.* 269: 30081–30084, 1994.
Miyake, K. et al., *J. Exp. Med.* 172: 69–76, 1990.
Pilarski, L.M. et al., *Leuk, Lymp.* 14: 363–374, 1994.
Samuel, S.K. et al., *J. Cell. Biol.* 123: 750–758, 1993.
Shi, Y. et al. *J. Immunol. Methods* 164: 149–154, 1993.
Toole, B.P., *Curr. Opin. Cell Biol.* 2: 839–844, 1990.
Toole, B.P., *Conn. Tiss. Res.*, 10:93–100, 1982.
Turley, E.A. et al., *Exp. Cell Res.* 207: 277–282, 1993.
Turley, E.A. et al., *Blood* 81: 446–453, 1993.
Turley, E.A., *Cancer Met. Rev.* 11: 21–30, 1992.
Turley, E.A., *Cancer Met. Rev.* 11: 1–3, 1992.
Turley, E.A., *Cancer Met. Rev.* 3: 325–339, 1984.
Turley, E.A. et al., *J. Cell. Biol.* 112: 1041–1047, 1991.
Underhill, C.B. et al., *J. Biol. Chem.* 262: 13142–13146, 1987.
Weigel, P.H. et al., *Ciba Found. Symp.* 143 248–264, 1989.
Weigel, P.H. et al., *J. Theol. Biol.* 119: 219–234, 1986.
Wang, C. et al., *Gene* 174: 299–306, 1996.
Yang, B. et al., *J. Biol. Chem.* 268: 8617–8623, 1993.
Dutta, A.S., Small Peptides. Chemistry, Biology, and Chemical Studies. Elsevier Science Publishers, Amsterdam, 1993. The entire book, especially pp. 16–20, 299, 308.*

* cited by examiner

*Primary Examiner*—Yvonne Eyler
*Assistant Examiner*—Janet L. Andres
(74) *Attorney, Agent, or Firm*—Bereskin & Parr; Micheline Gravelle

(57) ABSTRACT

Novel hyaluronan-binding peptides are provided. The peptides are useful in preventing and treating disorders associated with altered tissue levels of hyaluronan or RHAMM, including cancer, inflammatory and autoimmune disorders and fibrotic disorders associated with tissue trauma.

12 Claims, 28 Drawing Sheets

Clones competed with unlabeled HA and sequenced

Phage 1: STMMSRSHKTRSHH
Phage 2: TMTRPHFHKRQLVLS

FIGURE 2A-F
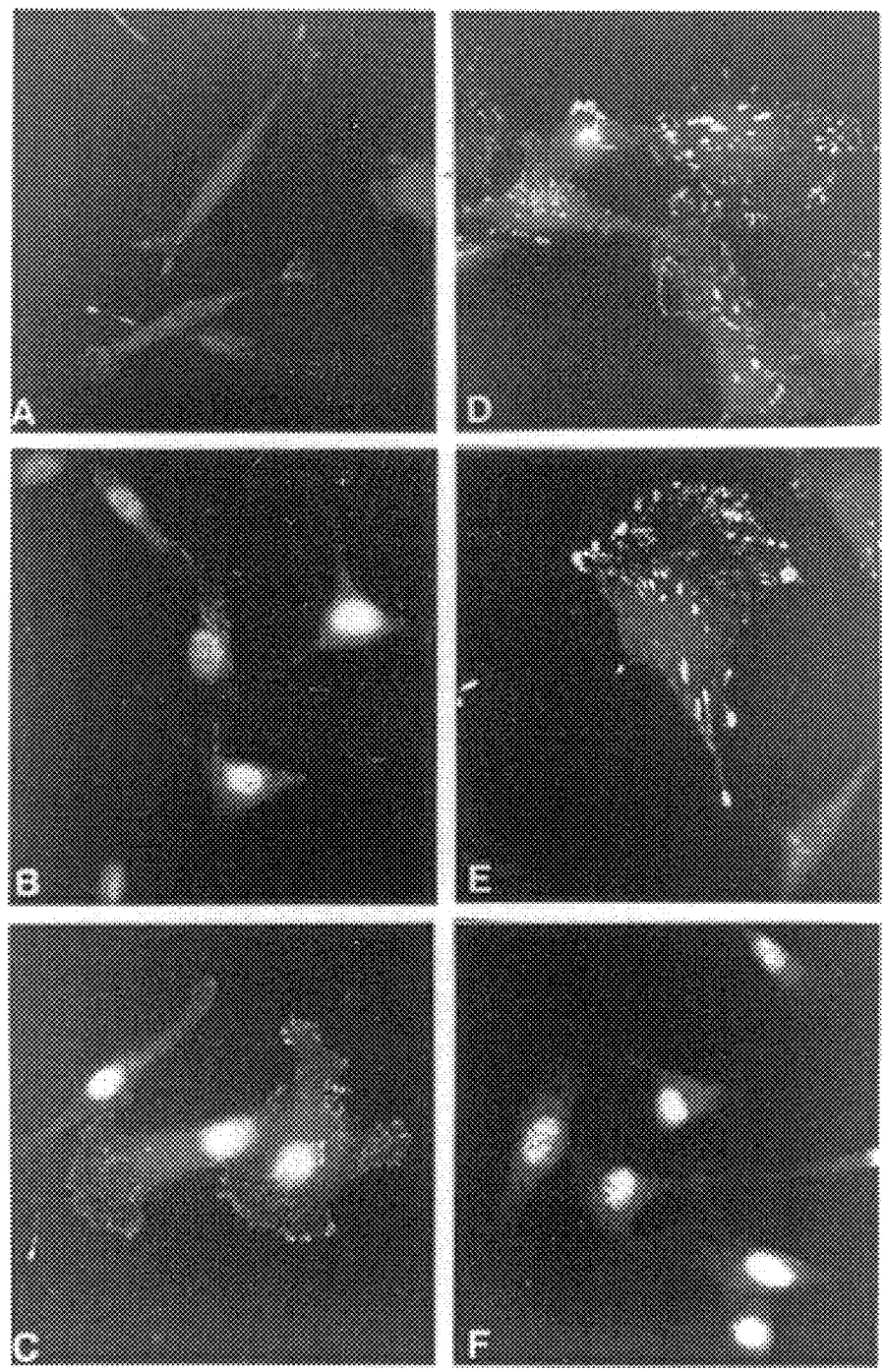

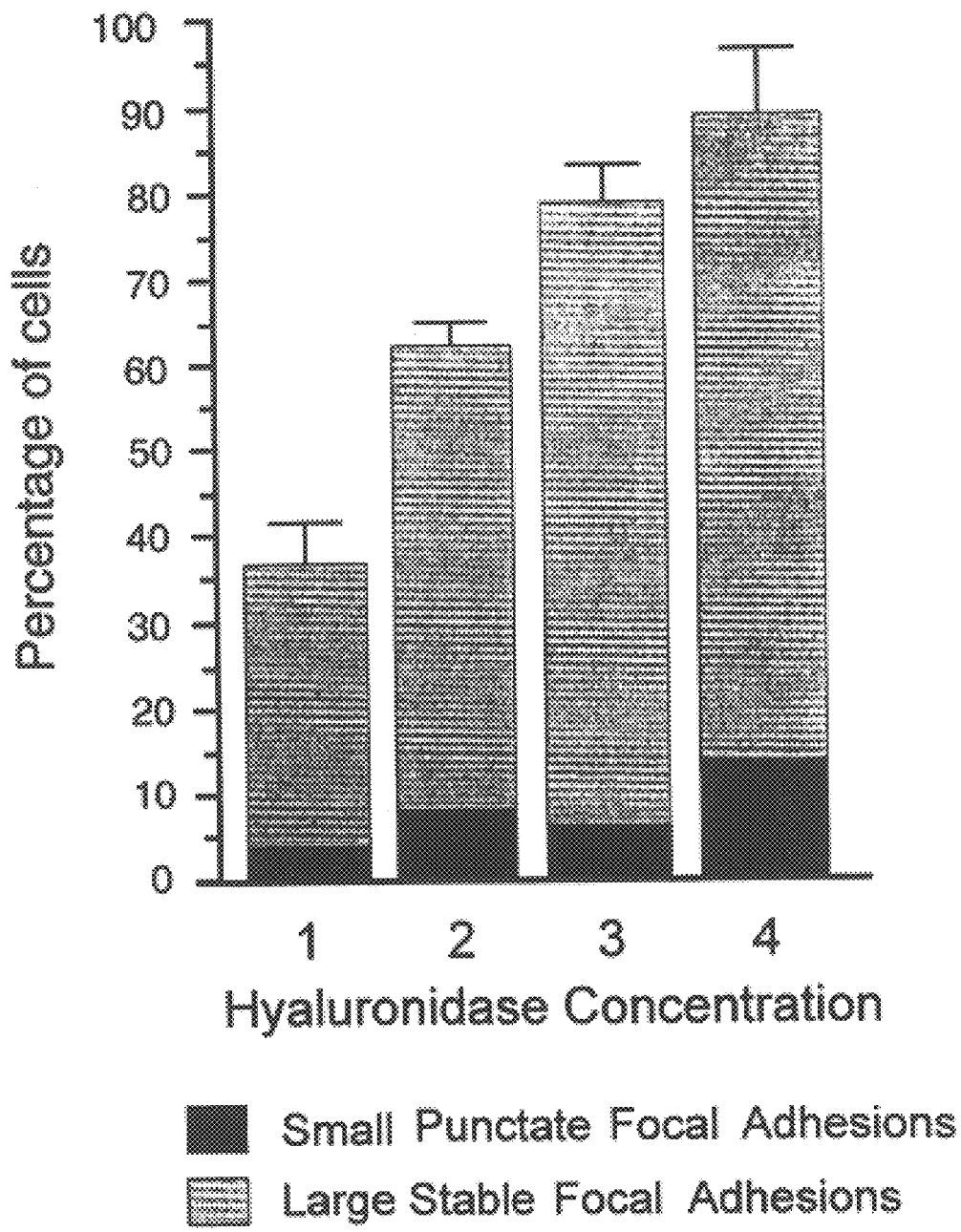

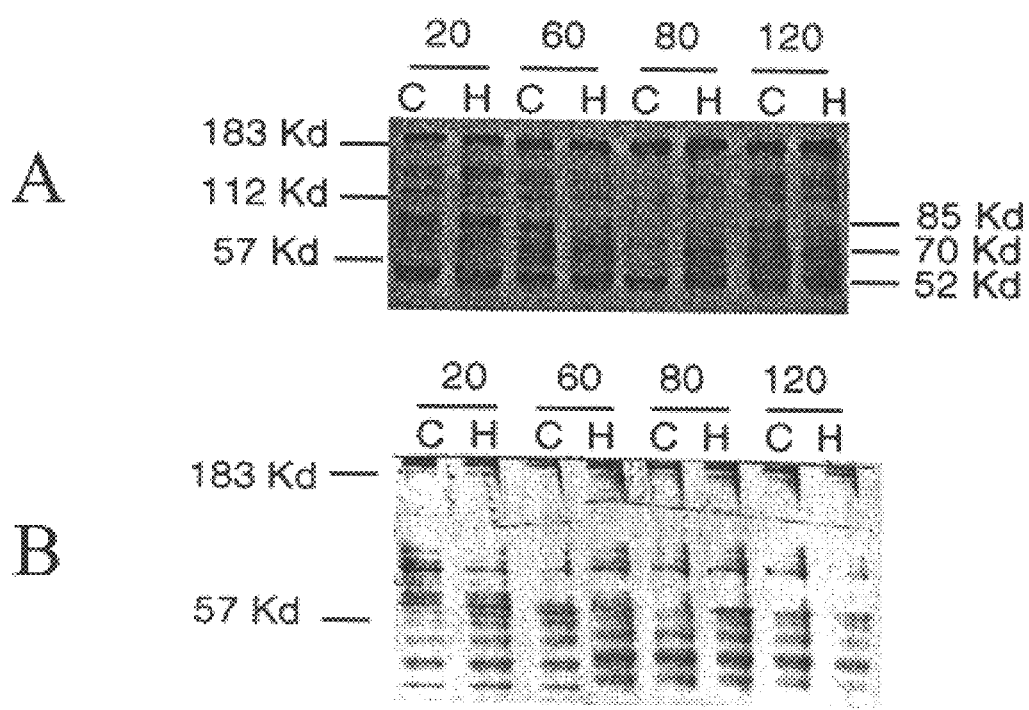
FIGURE 3A-B

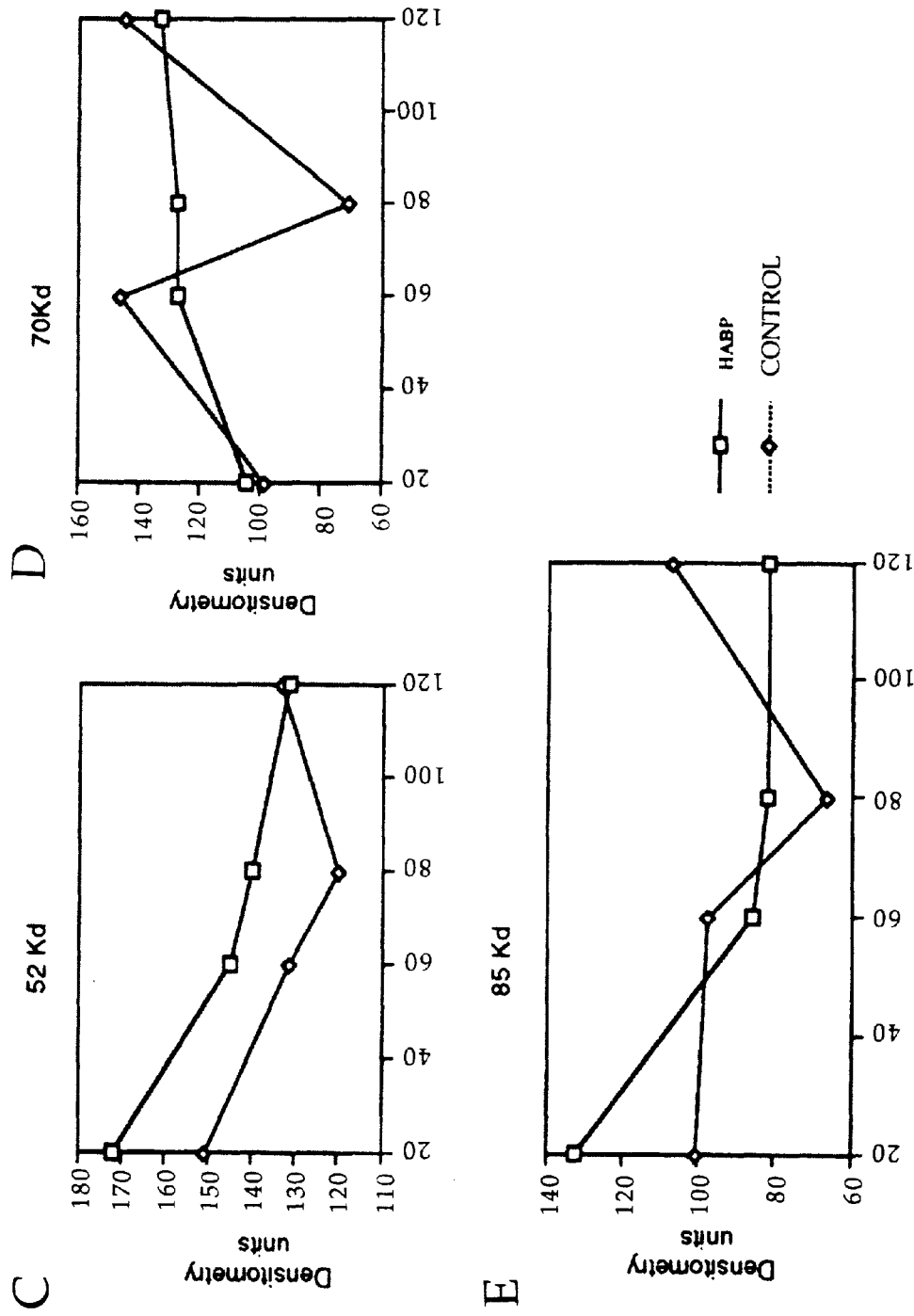
FIGURE 3C-E

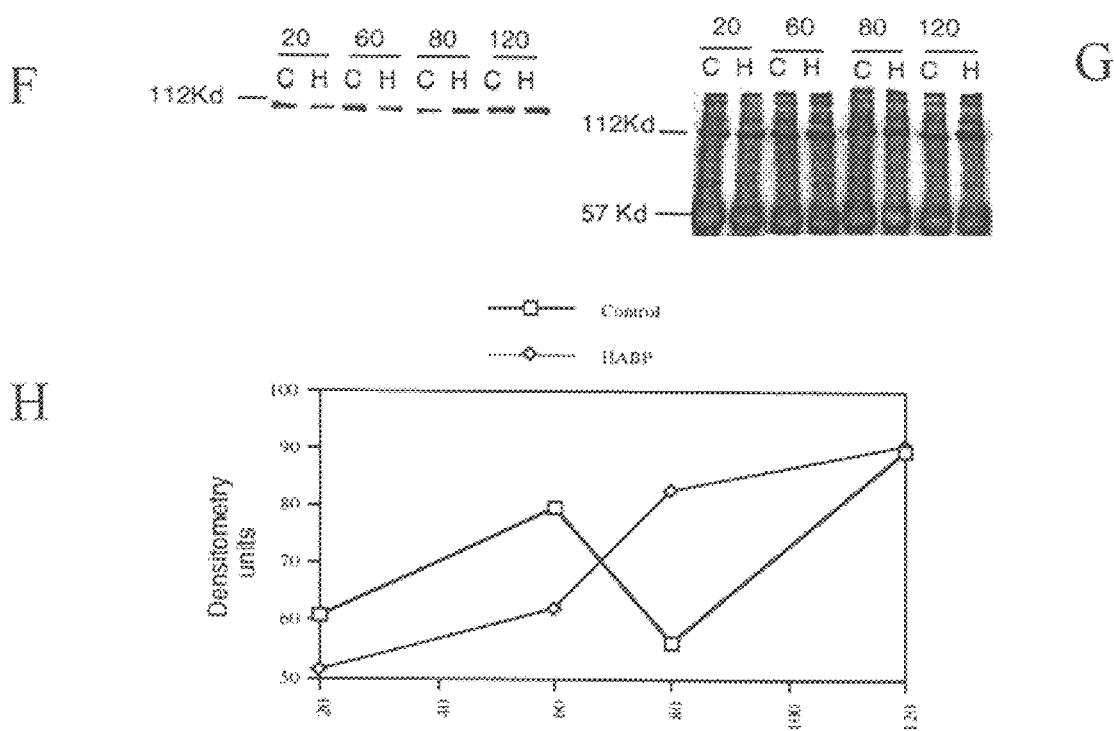
FIGURE 3F-H

FIGURE 7
A
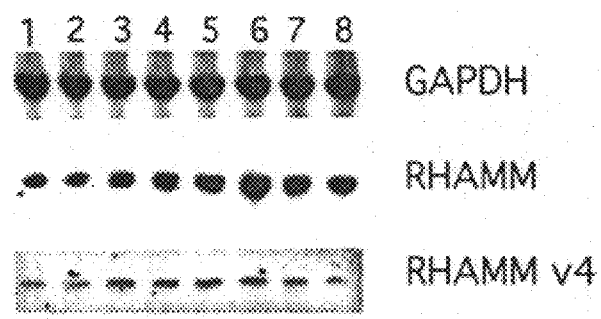
B
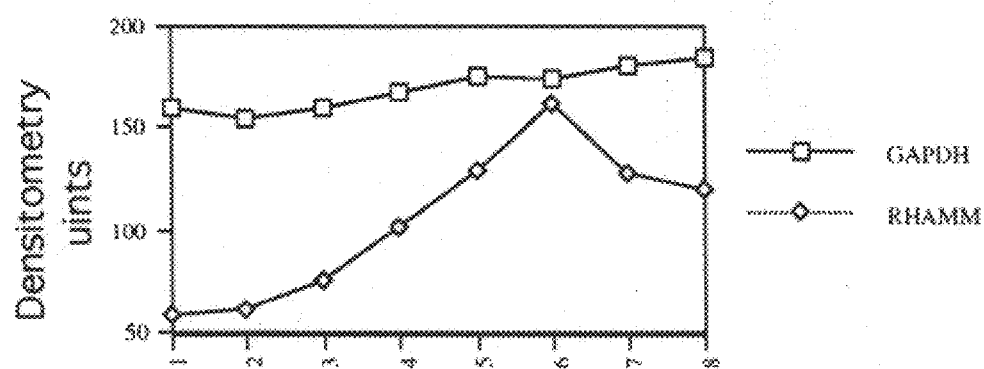

FIGURE 9A-D
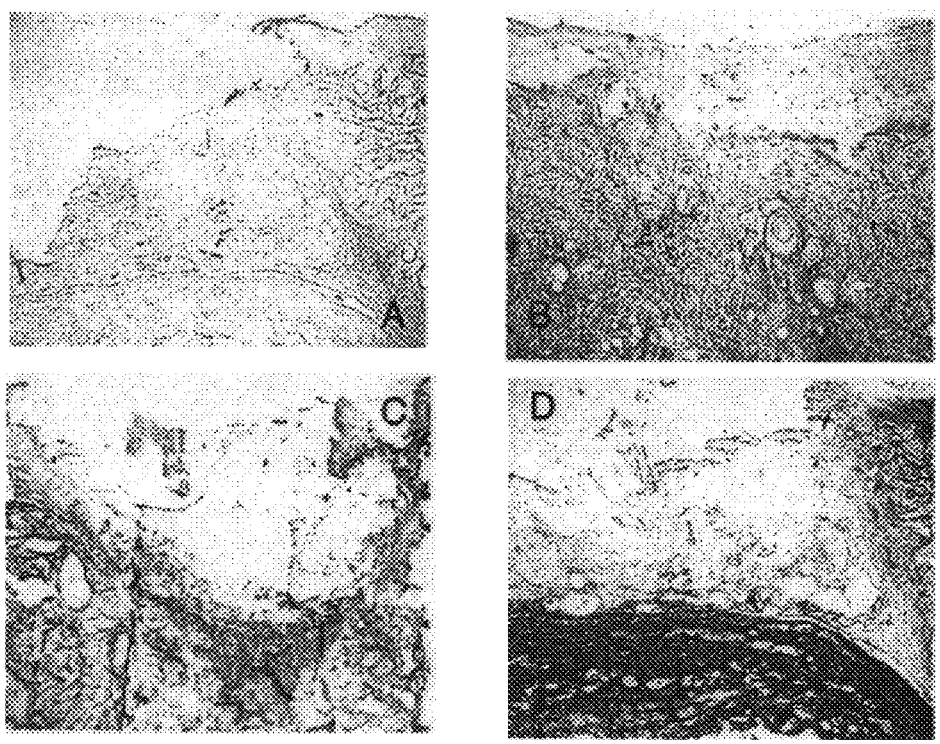

FIGURE 10A-B
A
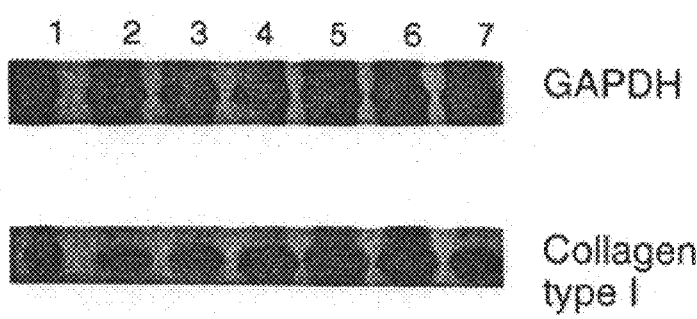
B
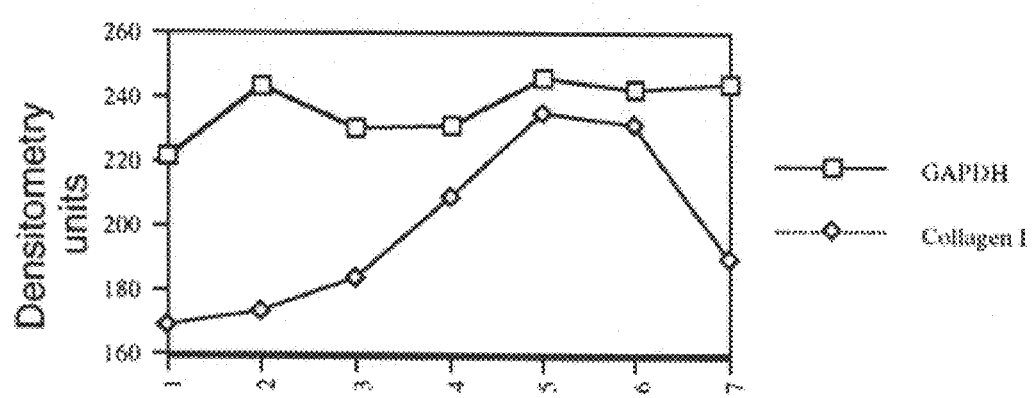

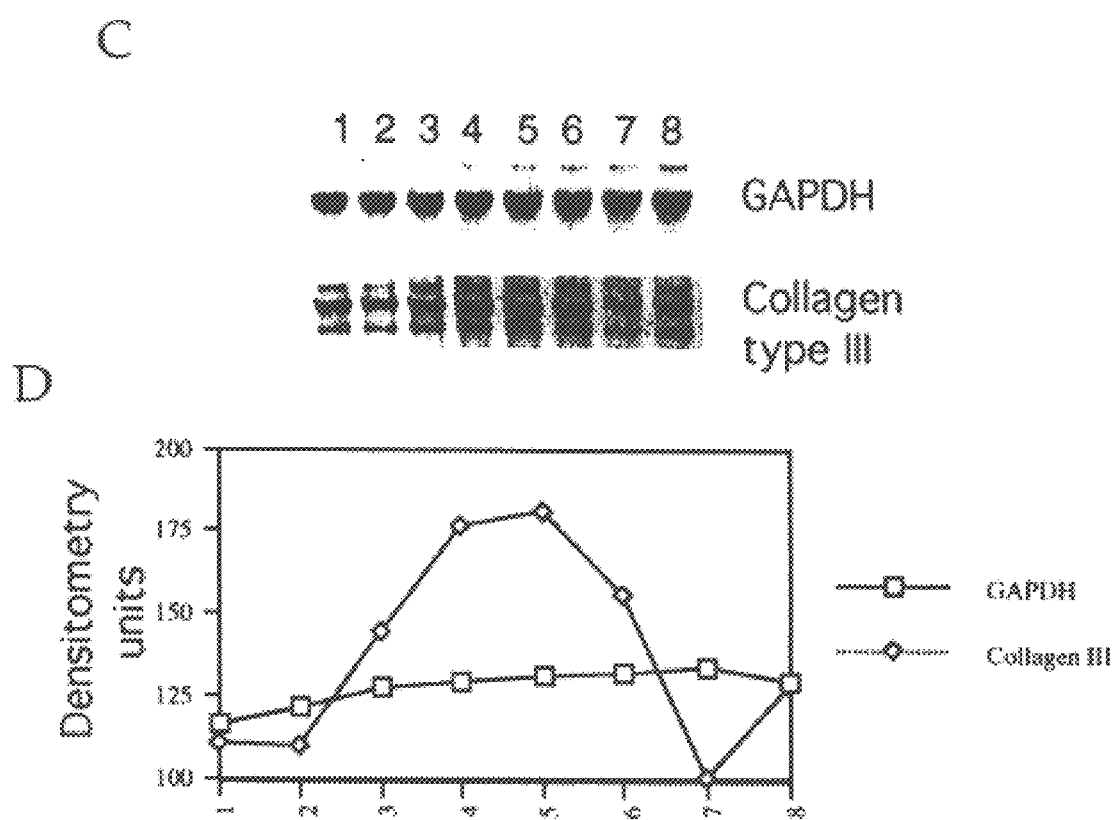
FIGURE 10C-D

FIGURE 16A-B
A
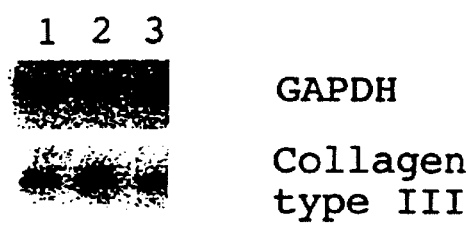
B
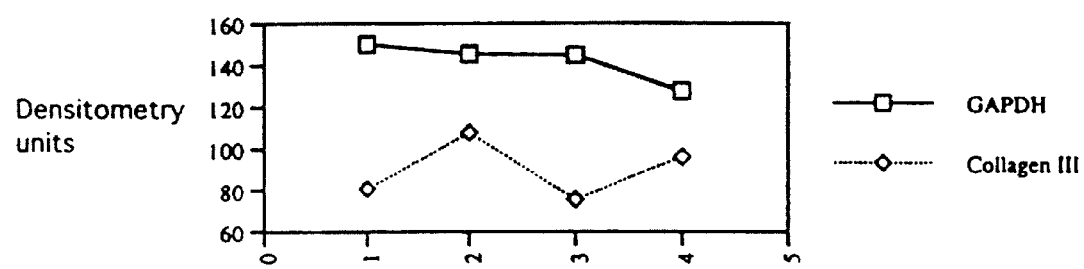

HUMAN FORESKIN FIBROBLASTS CONTRACTION

EFFECTS OF HA-BINDING PEPTIDE
(1 ng/mL and 500 ug/mL)

HUMAN FORESKIN FIBROBLASTS CONTRACTION

EFFECTS OF HA-BINDING PEPTIDE
(1 ng/mL to 500 ug/mL)

HUMAN FORESKIN FIBROBLASTS CONTRACTION

EFFECTS OF RHAMM-MOTIF PEPTIDE
(1 ng/mL to 500 ug/mL)

HUMAN FORESKIN FIBROBLASTS CONTRACTION

EFFECTS OF ANTI-EXON 5 ANTIBODY

HUMAN FORESKIN FIBROBLASTS CONTRACTION

EFFECTS OF ANTI-EXON 9 ANTIBODY

HUMAN FORESKIN FIBROBLASTS CONTRACTION

EFFECTS OF ANTI-CD44 ANTIBODY

SEQUENCE LISTING (1) GENERAL INFORMATION:

(iii) NUMBER OF SEQUENCES: 22

(2) INFORMATION FOR SEQ ID NO:1:

(i) SEQUENCE CHARACTERISTICS:
      (A) LENGTH: 15 amino acids
      (B) TYPE: amino acid
      (C) STRANDEDNESS: single
      (D) TOPOLOGY: linear (ii) MOLECULE TYPE: peptide (xi) SEQUENCE DESCRIPTION: SEQ ID NO:1:

Thr Met Thr Arg Pro His Phe His Lys Arg Gln Leu Val Leu Ser
1         5                 10               15

(2) INFORMATION FOR SEQ ID NO:2:

(i) SEQUENCE CHARACTERISTICS:
      (A) LENGTH: 15 amino acids
      (B) TYPE: amino acid
      (C) STRANDEDNESS: single
      (D) TOPOLOGY: linear (ii) MOLECULE TYPE: peptide (xi) SEQUENCE DESCRIPTION: SEQ ID NO:2:

```
Ser Thr Met Met Ser Arg Ser His Lys Thr Arg Ser Cys His His
1               5                   10                  15
```

(2) INFORMATION FOR SEQ ID NO:3:

(i) SEQUENCE CHARACTERISTICS:
        (A) LENGTH: 14 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:3:

```
Ser Thr Met Met Ser Arg Ser His Lys Thr Arg Ser His His
1               5                   10
```

(2) INFORMATION FOR SEQ ID NO:4:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:4:

```
Ser Thr Met Met Ser Arg Ser His Lys Thr Arg Ser His His Val
1               5                   10                  15
```

(2) INFORMATION FOR SEQ ID NO:5:

(i) SEQUENCE CHARACTERISTICS:
        (A) LENGTH: 45 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO:5:

```
ACCATGACCC GTCCGCACTT CCACAAACGT CAGCTGGTTC TGTCT          45
```

(2) INFORMATION FOR SEQ ID NO:6:

(i) SEQUENCE CHARACTERISTICS:
        (A) LENGTH: 45 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO:6:

```
ACSATGACSC GSCCSCACTT CCACAAGCGS CAGCTSGTSC TSWSS          45
```

(2) INFORMATION FOR SEQ ID NO:7:

(i) SEQUENCE CHARACTERISTICS:
        (A) LENGTH: 45 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO:7:

TCTACCATGA TGTCTCGTTC TCACAAAACC CGTTCTCACC ACTGT                              45

(2) INFORMATION FOR SEQ ID NO:8:

(i) SEQUENCE CHARACTERISTICS:
        (A) LENGTH: 45 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO:8:

WSSACSATGA TGWSSCGSWS SCACAAGACS CGSWSSCACC ACTGC                              45

(2) INFORMATION FOR SEQ ID NO:9:

(i) SEQUENCE CHARACTERISTICS:
        (A) LENGTH: 42 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO:9:

TCTACCATGA TGTCTCGTTC TCACAAAACC CGTTCTCACC AC                                 42

(2) INFORMATION FOR SEQ ID NO:10:

(i) SEQUENCE CHARACTERISTICS:
        (A) LENGTH: 42 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO:10:

WSSACSATGA TGWSSCGSWS SCACAAGACS CGSWSSCACC AC                                 42

(2) INFORMATION FOR SEQ ID NO:11:

(i) SEQUENCE CHARACTERISTICS:
        (A) LENGTH: 45 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO:11:

TCTACCATGA TGTCTCGTTC TCACAAAACC CGTTCTCACC ACGTG                              45

(2) INFORMATION FOR SEQ ID NO:12:

(i) SEQUENCE CHARACTERISTICS:
        (A) LENGTH: 45 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO:12:

WSSACSATGA TGWSSCGSWS SCACAAGACS CGSWSSCACC ACGTC                              45

(2) INFORMATION FOR SEQ ID NO:13:

(i) SEQUENCE CHARACTERISTICS:
    (A) LENGTH: 21 base pairs
    (B) TYPE: nucleic acid
    (C) STRANDEDNESS: single
    (D) TOPOLOGY: linear (ii) MOLECULE TYPE: other nucleic acid (xi) SEQUENCE DESCRIPTION: SEQ ID NO:13:

GTAACCAACT GGGACGATAT B                                              21

(2) INFORMATION FOR SEQ ID NO:14:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO:14:

GATCTTGATC TTCATGGTGC T                                              21

(2) INFORMATION FOR SEQ ID NO:15:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO:15:

GGGTTAGTTA TGTTGGTTGG T                                              21

(2) INFORMATION FOR SEQ ID NO:16:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO:16:

CTGAAGATGA GCAGACAGTT C                                              21

(2) INFORMATION FOR SEQ ID NO:17:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO:17:

AATGGCCGCT ACAGTATCTC CAGGACTGAA                                     30

(2) INFORMATION FOR SEQ ID NO:18:

(i) SEQUENCE CHARACTERISTICS:
        (A) LENGTH: 30 base pairs
        (B) TYPE: nucleic acid

```
        (C) STRANDEDNESS: single
        (D) TOPOLOGY: linear (ii) MOLECULE TYPE: other nucleic acid (xi) SEQUENCE DESCRIPTION: SEQ ID NO:18:

GTTGATCACC AGCTTCTTCT TCTGCCCACA                                          30

(2) INFORMATION FOR SEQ ID NO:19:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO:19:

CCCACGTAGG TGTCCTAAAG T                                                   21

(2) INFORMATION FOR SEQ ID NO:20:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO:20:

CCGTGGTGCT AAAATAATAA A                                                   21

(2) INFORMATION FOR SEQ ID NO:21:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO:21:

CGAGGTAACA GAGGTGAAAG A                                                   21

(2) INFORMATION FOR SEQ ID NO:22:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO:22:

AACCCAGTAT TCTCCGCTCT T                                                   21
```

ENHANCED AFFINITY HYALURONAN BINDING PEPTIDES

This application claims the benefit under 35 USC§119(e) of U.S. provisional application serial No. 60/068,285, filed on Dec. 19, 1997.

FIELD OF THE INVENTION

The present invention relates to novel enhanced affinity hyaluronan binding peptides, to methods for modulating cell locomotion and for modulating physiological and pathological conditions involving cell locomotion utilizing the peptides of the invention and to pharmaceutical compositions containing the peptides.

BACKGROUND OF THE INVENTION

Hyaluronic acid or hyaluronan (HA) is a large negatively charged glucosaminoglycan consisting of repeating disaccharides of N-acetylglucosamine and -glucuronic acid. This polymer is ubiquitous in the extracellular matrix and is the major component of skin, cartilage and brain tissue. In addition to its known macrostructural functions, it also performs physicochemical functions, for example, by acting as a lubricant in the synovial fluid in joints.

Synthesis of HA has been associated with the morphogenesis of many tissues, with wound repair, tumour invasion and cellular immune function (Toole, B. P., *Connect. Tissue Res.* 10: 93–100, 1982; Pauli, B. V. et al., Cancer Met. Rev. 2: 129–152, 1983; Toole, B. P. et al., *Ciba Found. Symp.* 143: 150–169, 1989; Turley, E. A., *Cancer Met. Rev.* 3: 325–339, 1984; Iozzo, R. V., *Lab. Invest.* 53: 373–396, 1985; Weigel, P. H. et al., J. Theol. Biol. 119: 219–234, 1986; Weigel, P. H. et al., *Ciba Found. Symp.* 143 248–264, 1989; Boudreax, N. et al., *Dev. Biol.* 143: 235–247, 1991; Turley, E. A., *Cancer Met. Rev.* 11: 21–30, 1992). The underlying mechanism of action at the cellular level is believed to involve the ability of HA to elicit receptor-mediated alterations of cell motility. High affinity HA receptors have been identified and characterized on a variety of cell types and these are namely the receptor for hyaluronan mediated mobility (or RHAMM) (Turley, E. A. et al., *J. Cell. Biol.* 112: 1041–1047, 1991; Hardwick, C. et al., *J. Cell. Biol.* 117: 1343–1350, 1992; Yang, B. et al., J. *Biol. Chem.* 268: 8617–8623, 1993), intercellular adhesion molecule-1 (or ICAM-1) (McCourt, P. A. G. et al., *J. Biol. Chem.* 269: 30081–30084, 1994) and CD44 (Underhill, C. B. et al., *J. Biol. Chem.* 262: 13142–13146, 1987; Stamenkovic, I. et al., *Cell* 56: 1057–1062, 1989; Aruffo, A. et al., *Cell* 61: 1303–1313, 1990; Lesley, J. et al., *Exp. Cell Res.* 187: 224–233, 1990; Miyake, K. et al., *J. Exp. Med.* 172: 69–76, 1990). Both RHAMM and CD44 have been shown to be associated with cell locomotion, cell proliferation and differentiation. Other HA-binding proteins in the extracellular milieu have also been identified and they are namely link protein, aggrecan, versican, GHAP, collagen type VI and TSG-6.

In tissue trauma, an acute, transient increase in production of HA is observed which is accompanied by an increase in expression of HA receptors such as the receptor for hyaluronan mediated mobility (RHAMM) and CD44. The in vivo physiological implications of these molecular events has not been fully elucidated although an increased production of HA and its accumulation has been shown to regulate locomotion of fibroblasts, inflammatory cells and epidermal cells depending upon the concentration of HA used. Further, HA affects collagen fibril formation and white blood cell phagocytic function, peroxide generation and cytokine expression. Prior research studies have demonstrated that high concentrations of HA act as a RHAMM antagonist to injured tissues including skin burns, ulcers, ruptured tympanic membranes and abraded cornea by reducing tissue fibrosis (Goz, K. L. and Benfield, P., *Drugs* 47: 536, 1994; King, S. R. et al., *Surgery* 109: 76, 1991; Riquelme-Saquier, J. L., *Dev. Ophthamol.* 22: 50, 1991; Chung, J. H. et al., *Exp. Eye Res.* 48: 569, 1989; Hellstrom, S. and Laurent, C., *Acta Otolaryngol.* 442 (Suppl.): 54, 1987; Retanda, G. G., *Ital. Dermatol. Venereol.* 120: 71–75, 1985; Abatangelo, G. et al., *J. Surg. Res.* 35: 410, 1983). Fibrosis of adult tissues after trauma is a serious clinical problem that can result in pathologies including malfunction of tissues due to keloids, hypertrophic scars, anatomonic strictures, intra-abdominal adhesions, cirrhosis of the liver, neurological deficits following spinal cord injury, valvular heart diseases, burn-injured joints as well as failure of anastomosis and adhesions following surgery (Bleacher, J. C. et al., *Dermatologic Clinics* 11: 677–683, 1993; Clark, R. A. et al., *Am. J. Med. Sci.* 306: 42–48, 1993; Hebda, P. A. et al., *Dermatologic Clinics* 11: 685–696, 1993; Adzick, N. S. and Longaker, M. T., *Ann. Surg.* 215: 3–7, 1992; Folkman, J., *Ann. Surg.* 215: 1–2, 1992).

Antagonism of RHAMM by antibodies and peptides has also been demonstrated to inhibit HA-promoted cell locomotion (International application PCT/CA93/00158 published as WO 93/21312). For instance, HA-promoted fibroblast locomotion was inhibited by application of a polyclonal or monoclonal antibody against the HA-receptor complex (HARC).

Tumorigenesis is commonly manifested by an uncontrolled proliferation of cells, and the metastatic spread of tumour tissue is associated with the ability of these cells to locomote and invade. Oncogenes and tumour suppressor genes are important factors in the control of tumour cell growth, but extracellular matrix (ECM) molecules such as HA and their receptors also play significant roles. HA and RHAMM have been shown to regulate cell proliferation and differentiation and are implicated in cell transformation and tumour metastasis.

The transforming oncogene H-ras promotes cell locomotion by enhancing the formation and release of autocrine motility factors, growth factors and extracellular matrix (ECM) molecules such as HA (Toole, B. P., *Curr. Opin. Cell Biol.* 2: 839–844, 1990; Stoker, M. et al., *Biochim. Biophys. Acta* 1072: 81–102, 1991; Hardingham, T. E. and Fosang, A. J., *FASEB J.* 6: 861–870, 1992; Laurent, T. C. and Fraser, J. R. E., *FASEB J.* 6: 2397–2404, 1992; Pilarski, L. M. et al., *Leuk, Lymp.* 14: 363–374, 1994). Enhancement of ras-transformed cell locomotion by HA has been found to depend on the presence of a HA-receptor complex termed HARC occurring at the cell surface or released as soluble proteins (Hall, C. L. et al., *Cell* 82: 1–20, 1995; Hall, C. L. and Turley, E. A., *J. Neuro-Oncol.* 26: 221–229, 1995; Turley, E. A. et al., *Blood* 81: 446–453, 1993; Turley, E. A. et al., *Exp. Cell Res.* 207: 277–282, 1993; Turley, E. A., *Cancer Metast. Rev.* 11: 21–30, 1992; Turley, E. A. et al., *J. Cell Biol.* 112: 1041–1047, 1991). Turley et al. (*Exp. Cell Res.* 207: 277–282, 1993) reported that such HA-promoted cell locomotion was inhibited by monoclonal antibodies specific to RHAMM thereby implicating RHAMM as the major HA-binding component of HARC in tumorigenesis and metastasis.

Under normal physiological conditions, RHAMM is not detectable on B-lymphocytes found in the blood, spleen or lymph node. Among B-cell malignancies, RHAMM is overexpressed on most terminally differentiated B-cells from multiple myeloma bone marrows, certain non-Hodgkin's lymphomas, and splenic hairy leukemic cells (Turley, E. A. et al., *Blood* 81: 446–453, 1993; Masellis-Smith, A. et al., *Blood* 87: 1891–1899, 1996). RHAMM is also overexpressed in breast carcinoma cells (Turley, E. A. et al., *Exp. Cell Res.* 207: 277–282, 1993; Hall, C. L. & Turley, E. A., *J. Neuro-oncol.* 26: 221–229, 1995), and in combination with an increased level of HA, are responsible for their enhanced motility and metastasis. Administration of RHAMM-transfected cells into animals results in spontaneous metastasis and formation of lung tumour colonies.

RHAMM was one of the first HA receptors to be isolated and characterized at the biochemical and molecular levels. It is an N-linked glycoprotein that binds HA with high affinity (Kd: 1 nM) and specificity. Several isoforms of RHAMM with different subcellular distribution have been identified. Isoforms found intracellularly and on the plasma membrane are designated iRHAMM and pRHAMM, respectively, and the secreted isoform is designated sRHAMM. The molecular structure of the various RHAMM isoforms may be differentially regulated by phosphorylation and/or glycosylation statuses. The precise roles of the RHAMM isoforms have not been fully elucidated, but it is believed that pRHAMM and sRHAMM elicit opposite activities and the net functional behaviour of a HA-RHAMM interaction depends at least in part on the balance of pRHAMM versus sRHAMM expressed by the cells involved.

Yang, B. et al. (*J. Biol. Chem.* 268: 8617–8623, 1993) have identified two discrete HA binding domains in RHAMM that occur at the carboxyl terminus of the protein. These domains are the only HA binding regions in the receptor protein and they each contribute approximately equally to the HA binding ability of RHAMM. Mutation studies have revealed that Domain I contains two sets of two basic amino acid residues spaced seven amino acids apart are important for HA binding of the receptor. Similarly, Domain II contains a lysine residue at position 423 and arginine at position 431 also spaced seven amino acids apart which are critical for HA binding activity. Collectively, these data predicted a generic binding motif with a structure of $B^1$-$A_n$-$B^2$ representing a minimal binding requirement for HA and RHAMM. $B^1$ and $B^2$ are the same or different basic amino acid residues and $A_n$ is a peptide sequence containing seven or eight amino acid residues which are the same or different and are neutral or basic amino acids. This generic binding motif was also found to be present in CD44, link protein and all other HA binding proteins discovered to date.

A full-length murine RHAMM cDNA has been cloned successfully from a GT11 3T3 cDNA expression library (Hardwick, C. et al., *J. Cell Biol.* 117: 1343–1350, 1992). Immunoblot analyses of cell lysates using antibodies to peptides encoded in the cDNA reacted specifically reacted with RHAMM protein. Using a fragment of the clone DNA sequence, a mouse fibroblast genomic library was screened to clone the genomic RHAMM gene which spans at least 20 kb and comprises 14 exons ranging in size from 75 to 1099 bp (Entwistle, J. et al., *Gene* 163: 233–238, 1995).

Similarly, a human RHAMM cDNA clone was also isolated successfully by a combination of screening a human breast cDNA expression library with the murine RHAMM cDNA as well as 5' RACE and reverse transcription-polymerase chain reaction using messenger RNA from the human breast cell line MCF-10A (Wang, C. et al., *Gene* 174: 299–306, 1996). The full-length human RHAMM cDNA encodes for a 725 amino acid protein and shares a 85% homology with the murine transcripts, RHAMM v4. More importantly, the HA binding motif $B^1$-$A_n$-$B^2$ which is shown to be critical for the signalling capability of RHAMM is 100% conserved between human and mouse.

PCT published patent application no. WO 93/21312 to the present inventor describes short peptides of nine or ten amino acid residues which mimic the HA binding motif of RHAMM. These RHAMM peptides possess the ability to bind HA and share a common generic peptide sequence represented by $B^1$-$A_n$-$B^2$ as described above.

However, the published application discloses key restrictions associated with the sequence of these RHAMM peptides with respect to their HA binding affinity. For example, it is clear from the patent publication that if $A_n$ is a peptide sequence containing less than seven or greater than eight amino acid residues, HA binding affinity is lost. Acidic amino acids are incompatible with HA binding as substitution of neutral or basic amino acid residues by acidic amino acid residues also abolishes HA binding affinity. Moreover, the basic amino acid histidine at the carboxy-terminal end is not compatible with HA binding which is indicated by the fact that replacement of the carboxy-terminal lysine or arginine by histidine completely destroyed HA-binding ability of the RHAMM peptides. In particular, a peptide with the sequence KLRSQLVHHH was unable to bind to HA.

PCT published patent application no. WO 97/24111 to the present inventor also describes HA-binding peptides consisting of dextrorotatory, D-amino acids and their ability to bind naturally occuring hyaluronic acid in the body which prevents hyaluronic acid from stimulating its receptors. Correspondingly, through the inhibition of hyaluronic acid receptor activation, said D-forms of HA-binding peptides were speculated to be useful when combined with a second medicine or therapeutic agent such as a surfactant for the treatment of herpes infection, an anti-microbial agent for the treatment of mononucleosis, dimethyl sulphoxide for AIDS therapy, insulin for the treatment of diabetes and a calcium channel blocker for the treatment of hypertension.

The invention of WO 97/24111 is distinct from the peptides and uses of the present invention in two major respects. First, based on past empirical evidence, it is well known that many physiologically and therapeutically important peptides of similar sizes to the peptides of the present invention exhibit significant stereospecificity in their biological actions. In many instances, subsitution of L-amino acid(s) by D-amino acid(s) or vice versa resulted in peptides that produce physiological effects that are opposite to those originally observed. Such a seemingly straightforward change of one or more amino acid residue(s) by its enantiomeric counterpart(s) can therefore create peptides that have distinctly different therapeutic uses.

For example, vasopressin is a nonapeptide and substitution of L-amino acid residue(s) to D-amino acid residue(s) in the SK&F vasopressin analogs dramatically reversed their bioactivity as vasopressin agonists to vasopressin antagonists (Albrightson-Winslow, C. et al., *J. Pharmacol. Exp. Ther.* 256: 335–340, 1991; Brooks, D. P. et al., *Eur. J. Pharmacol.* 160: 159–152, 1989). Similarly, enantiomeric substitutions of L- and D-amino acids in substance P, an undecapeptide, also dramatically changed its agonistic and antagonistic activities as well as the peptide's specificity to stimulate different receptor subtypes and to elicit totally different physiological responses (Cross, M. et al., *Eur. J. Pharmacol.* 291: 291–300, 1995; Dutta, A. S. et al., *J. Med. Chem.* 29:1163–1171, 1986; Dutta, A. S. et al., *J. Med. Chem.* 29:1171–1178, 1986). To further illustrate this phenomen, substance P with an L-proline at position 9 induced a marked scratching response in the rat but does not produce any response in colon smooth muscle. Conversely, substitution of this single amino acid by a D-proline resulted in a peptide that elicited no scratching response but produced sigificant contraction of colon smooth muscle (Piercey, M. F. et al., *Life Sci.* 36: 777–780, 1985).

Similarly, Casteels, P. and Tempst, P. reported the stereospecific requirements of apidaecin-type antibacterial peptides in which the L-enantiomer of apidaecin is a lethal non-poreforming bacteriotoxin but the D-enantiomer is completely devoid of antibacterial activity (Casteels, P. and Tempst, P., *Biochem. Biophys. Res. Commun.* 199: 339–345, 1994). Oren, Z. et al. also reported the detrimental effects of D-amino acid substitution on the alpha-helical structure of diastereomeric dodecapeptides and their antibacterial effects (Oren, Z. et al., *J. Biol. Chem.* 272: 14643–14649, 1997).

Furthermore, peptidyl dipeptide hydrolase catalyzes the hydrolysis of the decapeptide angiotensin I to the physiologically active octapeptide angiotensin II. This enzyme has been shown to exhibit an absolute stereospecific requirement for L-amino acid residues at the C-terminus of the angiotensin I peptide in order to achieve activation (Oshima, G. and Nagasawa, K., *J. Biochem.* 86: 1719–1724, 1979; Oparil, S. et al., *Circ. Res.* 29: 682–690, 1971).

In view of the above, the biological activities of one enantiomer of a given peptide are quite distinct from those of another enantiomer of the same peptide. The speculation of certain activities for the D-forms of the HA-binding peptides in WO 97/24111 therefore cannot be used to predict the clinical utilities of the L-forms of said peptides. This is supported by the fact that the L-peptides of the present invention, when given alone, are useful in the prevention of skin tissue fibrosis which is clearly in contrast to the combinational therapeutic regimens and the therapeutic areas described in WO 97/24111.

Second, notwithstanding the terminology "HA-binding peptides" and that the actions of the D-peptides in WO 97/24111 depend on their ability to inhibit HA interaction with its receptors, the L-forms of the peptides of the present invention do not elicit its biological actions by inhibiting HA interaction with its receptors (RHAMM and CD44). This aspect of the invention is demonstrated in greater detail below.

SUMMARY OF THE INVENTION

The present inventor has isolated novel peptides which can bind hyaluronic acid (HA) or hyaluronan with enhanced affinity. The peptides of the present invention differ from the previous HA-binding peptides and do not fall within the previously described formula.

In one embodiment, the present invention provides a HA-binding peptide comprising a sequence of the formula I:

$$X_1-X_2-X_1-X_3-X_4-X_3-X_4-X_3-X_3-X_3-X_5-X_6-X_6-X_6-X_1$$

wherein
each $X_1$ is independently selected from a hydroxy amino acid residue;
each $X_2$ is independently selected from a sulfur containing amino acid residue;
each $X_3$ is independently selected from a basic amino acid residue;
each $X_4$ is independently selected from an imino or aromatic amino acid residue;
each $X_5$ is independently selected from a dicarboxylic acid amino acid residue; and
each $X_6$ is independently selected from an aliphatic amino acid residue, and fragments, analogs or derivatives of the peptide which can bind HA.

In a preferred embodiment, the present invention provides a HA-binding peptide comprising a sequence of the formula I:

$$X_1-X_2-X_1-X_3-X_4-X_3-X_4-X_3-X_3-X_3-X_5-X_6-X_6-X_6-X_1$$

wherein
each $X_1$ is independently selected from threonine or serine;
each $X_2$ is independently selected from methionine or cysteine;
each $X_3$ is independently selected from arginine, lysine or histidine;
each $X_4$ is independently selected from proline, phenylalanine or tryptophan;
each $X_5$ is independently selected from asparagine or glutamine; and
each $X_6$ is independently selected from leucine, isoleucine, valine or alanine, and fragments, analogs or derivatives of the peptide which can bind HA.

A preferred peptide of Formula I is TMTRPHFH-KRQLVLS (SEQ.ID.NO.:1).

In another embodiment, the present invention provides a HA-binding peptide comprising a sequence of the Formula II:

$$Y_1-Y_1-Y_2-Y_2-Y_1-Y_3-Y_1-Y_3-Y_3-Y_1-Y_3-Y_1-Y_2-Y_3-Y_3$$

wherein
each $Y_1$ is independently selected from a hydroxy amino acid residue;
each $Y_2$ is independently selected from a sulfur containing amino acid residue; and
each $Y_3$ is independently selected from a basic amino acid residue, and fragments, analogs or derivatives of the peptide which bind HA.

In a preferred embodiment, the present invention provides a HA-binding peptide comprising a sequence of the Formula II:

$$Y_1-Y_1-Y_2-Y_2-Y_1-Y_3-Y_1-Y_3-Y_3-Y_1-Y_3-Y_1-Y_2-Y_3-Y_3$$

wherein
each $Y_1$ is independently selected from serine or threonine;
each $Y_2$ is independently selected from methionine or cysteine; and
each $Y_3$ is independently selected from arginine, lysine or histidine, and fragments, analogs or derivatives of the peptide which bind HA.

A preferred peptide of the Formula II is STMMSRSHK-TRSCHH (SEQ.ID.NO.:2).

In another embodiment, the present invention provides a HA-binding peptide comprising a sequence of the Formula III:

$$Z_1-Z_1-Z_2-Z_2-Z_1-Z_3-Z_1-Z_3-Z_3-Z_1-Z_3-Z_1-Z_3-Z_3$$

wherein
each $Z_1$ is independently selected from a hydroxy amino acid residue;
each $Z_2$ is independently selected from a sulfur containing amino acid residue; and each $Z_3$ is independently selected from a basic amino acid residue, and fragments, analogs or derivatives of the peptide which bind HA.

In a preferred embodiment, the present invention provides a HA-binding peptide comprising a sequence of the Formula III:

$$Z_1\text{-}Z_1\text{-}Z_2\text{-}Z_2\text{-}Z_1\text{-}Z_3\text{-}Z_1\text{-}Z_3\text{-}Z_3\text{-}Z_1\text{-}Z_3\text{-}Z_1\text{-}Z_3\text{-}Z_3$$

wherein each $Z_1$ is independently selected from serine or threonine;

each $Z_2$ is independently selected from methionine or cysteine; and each $Z_3$ is independently selected from arginine, lysine or histidine, and fragments, analogs or derivatives of the peptide which bind HA.

A preferred peptide of the Formula III is STMMSRSHKTRSHH (SEQ.ID.NO.:3). A peptide of the Formula III may optionally contain a valine residue at the C-terminal and have the following sequence: STMMSRSHKTRSHHV (SEQ.ID.NO.:4).

The term "HA-binding peptide" as used herein means a peptide that can bind hyaluronic acid (or hyaluronan) and is of the Formula I, II, or III as defined above. The term includes fragments, analogs and derivatives of the peptides which maintain the ability to bind HA. Collectively, the HA binding peptides defined herein are referred to as "the peptides of the invention". Preferably, the peptides of the invention consist of amino acids in the levorotatory (L) form which corresponds to how amino acids occur in nature.

The present invention also provides a purified and isolated nucleic acid having a nucleotide sequence encoding an HA-binding peptide comprising a sequence of the formula I, II or III described above. The present invention also provides an expression vector comprising a DNA molecule encoding the HA-binding peptide adapted for transfection or transformation of a host cell.

In a further aspect, the present invention provides a pharmaceutical composition containing one or more HA-binding peptides or nucleic acid molecules encoding a HA-binding peptide of the invention in admixture with a pharmaceutically acceptable carrier, diluent or excipient for modulating cell locomotion and for the prophylaxis or treatment of cancer, inflammatory and autoimmune disorders and fibrotic disorders associated with tissue trauma and its recovery.

The invention also contemplates a method for preventing or treating cancer, inflammatory and autoimmune disorders and fibrotic disorders associated with tissue trauma and its recovery by administering an effective amount of one or more HA-binding peptides or nucleic acid molecules encoding a HA-binding peptide to an animal in need thereof.

Other objects, features and advantages of the present invention will become apparent from the following detailed description and attached drawings. It should be understood, however, that the detailed description and associated examples are given by way of illustration only, and various changes and modifications thereto falling within the scope of the invention will become apparent to those skilled in the art. In addition, reference is made herein to various publications, patents and patent applications which are hereby incorporated by reference in their entirety.

BRIEF DESCRIPTION OF THE DRAWINGS

The invention will be better understood with reference to the drawings in which:

FIG. 1 is a schematic diagram illustrating the isolation of enhanced affinity hyaluronan binding peptides from a 15-mer phage display library.

FIGS. 2A–F illustrates the stimulation of focal contact formation by enhanced affinity hyaluronan binding peptides.

FIG. 2G is a graph illustrating the formation of vinculin-positive focal contacts in ras-transformed 10T 1/2 fibroblast versus the concentration of hyaluronidase.

FIG. 3A is a Western blot of the data from image analysis on the inhibition of cell motility fluctuations on fibronectin substrata by enhanced affinity hyaluronan binding peptides.

FIG. 3B is an SDS-PAGE lf the data from image analysis on the inhibition of cell motility fluctuations on fibronectin substrata by enhanced affinity hyaluronan binding peptides.

FIGS. 3C–3E shows the densitometry analysis of the data in the Western blot in FIG. 3A.

FIG. 3F is a Western blot of the data illustrating that fluctuations in cell motility is correlated with fluctuations in protein tyrosine phosphorylation and that addition of enhanced affinity hyaluronan binding peptides reduced protein phosphorylation/dephosphorylation cycles;

FIG. 3G shows Coomassie blue staining of lysate proteins separated by SDS-PAGE;

FIG. 3H shows densitometry data of Western blots in FIG. 3F;

FIG. 3I shows inhibition of cell motility fluctuations by enhanced affinity hyaluronan binding peptides for over 18 h as compared to null effect by the scrambled peptides (controls).

FIG. 4 presents data from RT-PCR analysis showing increases in RHAMM and CD44 mRNA at 24 h after injury.

FIG. 5 shows data from immunohistochemical analysis showing expression of RHAMM (A) immediately after injury (B) 24 h after injury (C) 48–72 h after injury (D) represents a biopsy site stained with IgG at 24 h after injury.

FIG. 6 presents (A) Western analysis data and (B) densitometry analysis data showing the presence of 3 major RHAMM isoforms (80 kDa, 68–70 kDa and 60 kDa proteins) in uninjured skin (1).

FIG. 7 shows (A) RT-PCR analysis data and (B) densitometry analysis data illustrating increases in mRNA for total RHAMM isoforms (designated RHAMM) and for RHAMM v4 (an isoform implicated in regulation of cell motility and growth) 6 h after injury (3).

FIG. 8 is a graph illustrating the concentrating of HA versus time after injury.

FIGS. 9A–D illustrates immunohistochemical data on distribution of HA in wound tissue.

FIGS. 10A and B shows results of (A) RT-PCR and (B) densitometry analyses of collagen type I mRNA. The times post injury are: (3) 48 h (4) 72 h, (5) 96 h, (6) 120 h and (7) 2 weeks.

FIGS. 10C and D shows results of (C) RT-PCR and (D) densitometry analyses of collagen type III mRNA. Collagen type III mRNA was present within uninjured skin at low levels (1) and increased at 6 h after injury (3) which reached a maximum at 12–24 h (4, 5) and declined thereafter. By 407 days post injury (7,8), collagen type III mRNA returned to background levels.

FIG. 11 is a graph showing glucosaminidase levels in wounds versus time after injury.

FIG. 12 shows data from histological analysis of wound site at 24 h after injury treated with (I) Vehicle or scrambled peptide (control); (II) HA binding peptides; (III) IgG antibodies and (IV) anti-RHAMM antibodies.

FIG. 13 is a graph showing the number of macrophages at the wound site in the presence of a HA binding peptides, scrambled peptides and untreated.

FIG. 14 is a graph showing that the HA binding peptides reduced glucosaminidase activity at the wound site in a dose-dependent manner as compared to the null effect of the scrambled peptide.

FIG. 15 shows the effect of the HA binding peptides on collagen type I mRNA levels as detected by RT-PCR analysis. Collagen type I mRNA levels increased by 72 h after injury (2, 3) above control levels with vehicle (1) or scrambled peptide (3). Wounds treated with enhanced affinity HA binding peptide exhibited low collagen type I mRNA levels (5).

FIGS. 16A and B shows the results of (A) RT-PCR and (B) densitometry analyses of the effect of the HA binding peptides on collagen type III mRNA levels as detected by RT-PCR analysis. Collagen type III mRNA levels was low in uninjured skin but were increased at 24 h after injury in wounds treated with vehicle and scrambled peptide (2). Wounds treated with the HA binding peptide exhibited low collagen type III mRNA levels (3).

DETAILED DESCRIPTION OF THE INVENTION

Figure 1:
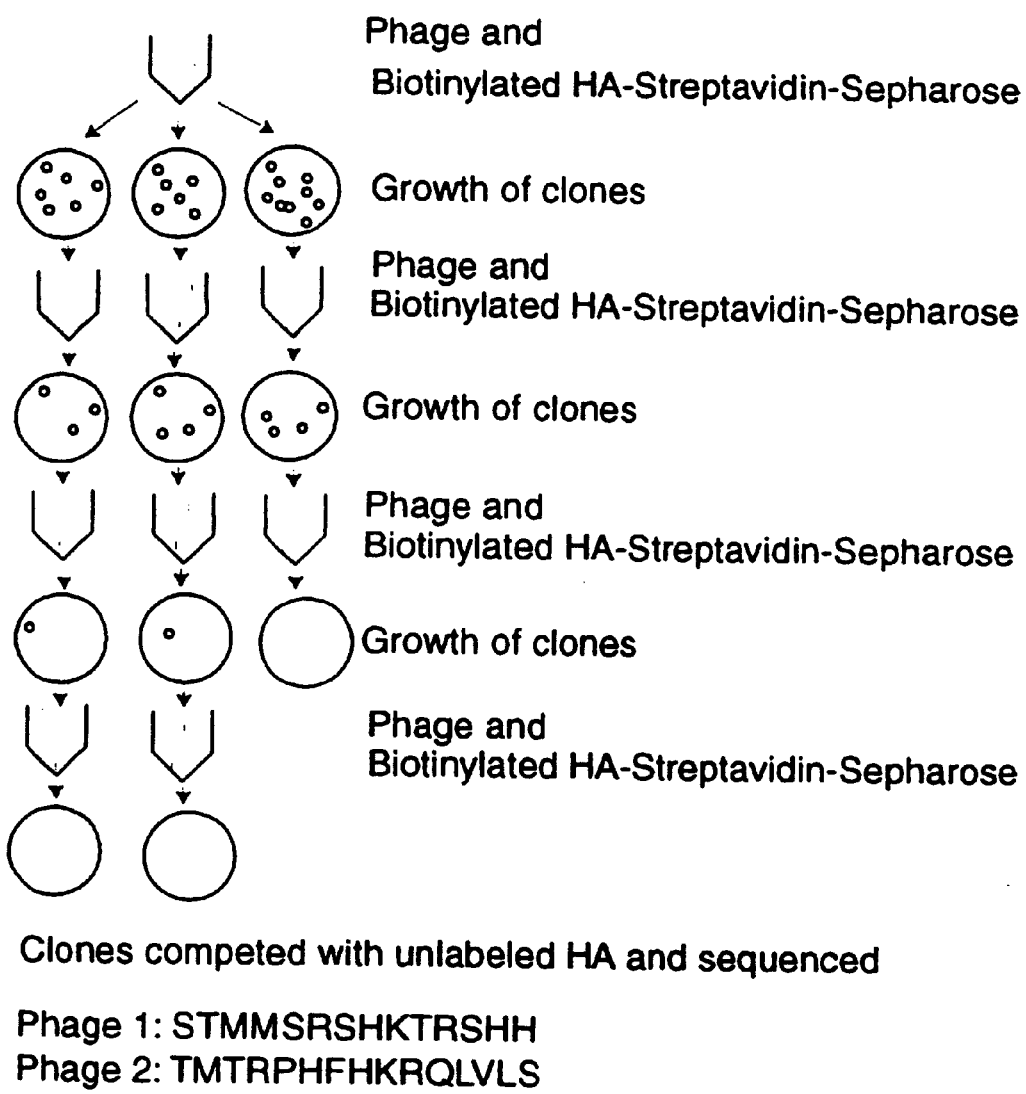

The following standard one letter and three letter abbreviations for the amino acid residues may be used throughout the specification: A, Ala—alanine; R, Arg—Arginine; N, Asn—Asparagine; D, Asp—Aspartic acid; C, Cys—Cysteine; Q, Gln—Glutamine; E, Glu—Glutamic acid; G, Gly—Glycine; H, His—Histidine; I, Ile—Isoleucine; L, Leu—Leucine; K, Lys—Lysine; M, Met—Methionine; F, Phe—Phenylanine; P, Pro—Proline; S, Ser—Serine; T, Thr—Threonine; W, Trp—Tryptophan; Y, Tyr—Tyrosine; and V, Val—Valine;

HA Binding Peptides

The present inventor has isolated, sequenced and characterized novel peptides of about 14 or 15 amino acid residues which bind hyaluronic acid or hyaluronan with enhanced affinity.

In one embodiment, the present invention provides a HA-binding peptide comprising a sequence of the formula I:

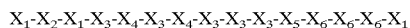

wherein
each $X_1$ is independently selected from a hydroxy amino acid residue;
each $X_2$ is independently selected from a sulfur containing amino acid residue;
each $X_3$ is independently selected from a basic amino acid residue;
each $X_4$ is independently selected from an imino or aromatic amino acid residue;
each $X_5$ is independently selected from a dicarboxylic acid amino acid residue; and
each $X_6$ is independently selected from an aliphatic amino acid residue, and fragments, analogs or derivatives of the peptide which can bind HA.

In a preferred embodiment, the present invention provides a HA-binding peptide comprising a sequence of the formula I:

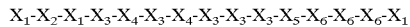

wherein
each $X_1$ is independently selected from threonine or serine;
each $X_2$ is independently selected from methionine or cysteine;
each $X_3$ is independently selected from arginine, lysine or histidine;
each $X_4$ is independently selected from proline, phenylalanine or tryptophan;
each $X_5$ is independently selected from asparagine or glutamine; and
each $X_6$ is independently selected from leucine, isoleucine, valine or alanine, and fragments, analogs or derivatives of the peptide which can bind HA.

A preferred peptide of Formula I is TMTRPHFH-KRQLVLS (SEQ.ID.NO.:1).

In another embodiment, the present invention provides a HA-binding peptide comprising a sequence of the Formula II:

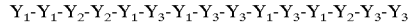

wherein
each $Y_1$ is independently selected from a hydroxy amino acid residue;
each $Y_2$ is independently selected from a sulfur containing amino acid residue; and
each $Y_3$ is independently selected from a basic amino acid residue, and fragments, analogs or derivatives of the peptide which bind HA.

In a preferred embodiment, the present invention provides a HA-binding peptide comprising a sequence of the Formula II:

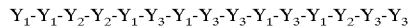

wherein
each $Y_1$ is independently selected from serine or threonine;
each $Y_2$ is independently selected from methionine or cysteine; and each $Y_3$ is independently selected from arginine, lysine or histidine, and fragments, analogs or derivatives of the peptide which bind HA.

A preferred peptide of the Formula II is STMMSRSHK-TRSCHH (SEQ.ID.NO.:2).

In another embodiment, the present invention provides a HA-binding peptide comprising a sequence of the Formula III:

$$Z_1\text{-}Z_1\text{-}Z_2\text{-}Z_2\text{-}Z_1\text{-}Z_3\text{-}Z_1\text{-}Z_3\text{-}Z_3\text{-}Z_1\text{-}Z_3\text{-}Z_1\text{-}Z_3\text{-}Z_3$$

wherein each $Z_1$ is independently selected from a hydroxy amino acid residue;

each $Z_2$ is independently selected from a sulfur containing amino acid residue; and each $Z_3$ is independently selected from a basic amino acid residue, and fragments, analogs or derivatives of the peptide which bind HA.

In a preferred embodiment, the present invention provides a HA-binding peptide comprising a sequence of the Formula III:

$$Z_1\text{-}Z_1\text{-}Z_2\text{-}Z_2\text{-}Z_1\text{-}Z_3\text{-}Z_1\text{-}Z_3\text{-}Z_3\text{-}Z_1\text{-}Z_3\text{-}Z_1\text{-}Z_3\text{-}Z_3$$

wherein each $Z_1$ is independently selected from serine or threonine;

each $Z_2$ is independently selected from methionine or cysteine; and each $Z_3$ is independently selected from arginine, lysine or histidine, and fragments, analogs or derivatives of the peptide which bind HA.

A preferred peptide of the Formula III is STMMSRSH-KTRSHH (SEQ.ID.NO.:3). A peptide of the Formula III may optionally contain a valine residue at the C-terminal and have the following sequence: STMMSRSHKTRSHHV (SEQ.ID.NO.:4).

The term "HA-binding peptide" as used herein means peptide that can bind hyaluronic acid (or hyaluronan) and is of the Formula I, II, or III as defined above. The term includes fragments, analogs and derivatives of the peptides which maintain the ability to bind HA. Collectively, the HA binding peptides defined herein are referred to as the peptides of the invention. Preferably, the peptides of the invention consist of amino acids in the levorotatory (L) form which corresponds to how amino acids occur in nature.

The term "analog" includes any peptide having an amino acid residue sequence substantially identical to the sequence of the HA binding peptides shown in Formula I, II, or III shown herein in which one or more residues have been conservatively substituted with a functionally similar residue and which displays the ability to mimic a HA binding peptide. Examples of conservative substitutions include the substitution of one non-polar (hydrophobic) residue such as alanine, isoleucine, valine, leucine or methionine for another, the substitution of one polar (hydrophilic) residue for another such as between arginine and lysine, between glutamine and asparagine, between glycine and serine, the substitution of one basic residue such as lysine, arginine or histidine for another, or the substitution of one acidic residue, such as aspartic acid or glutamic acid for another. The phrase "conservative substitution" also includes the use of a chemically derivatized residue in place of a non-derivatized residue provided that such polypeptide displays the requisite activity.

"Derivative" refers to a peptide having one or more residues chemically derivatized by reaction of a functional side group. Such derivatized molecules include for example, those molecules in which free amino groups have been derivatized to form amine hydrochlorides, p-toluene sulfonyl groups, carbobenzoxy groups, t-butyloxycarbonyl groups, chloroacetyl groups or formyl groups. Free carboxyl groups may be derivatized to form salts, methyl and ethyl esters or other types of esters or hydrazides. Free hydroxyl groups may be derivatized to form O-acyl or O-alkyl derivatives. The imidazole nitrogen of histidine may be derivatized to form N-im-benzylhistidine. Also included as derivatives are those peptides which contain one or more naturally occurring amino acid derivatives of the twenty standard amino acids. For examples: 4-hydroxyproline may be substituted for proline; 5-hydroxylysine may be substituted for lysine; 3-methylhistidine may be substituted for histidine; homoserine may be substituted for serine; and ornithine may be substituted for lysine. HA-binding peptides of the present invention also include any peptide having one or more additions and/or deletions or residues relative to the sequence of a polypeptide whose sequence is shown herein, so long as the requisite activity is maintained or increased.

The term "fragment" refers to any subject peptide having an amino acid residue sequence shorter than that of a peptide whose amino acid residue sequence is shown herein.

The invention includes cyclic derivatives of the HA binding peptides of the invention. Cyclization allows the peptide to assume a more favourable conformation. Cyclization of the peptides may be achieved using techniques known in the art. In particular, disulphide bonds may be formed between two appropriately spaced components having free sulfhydryl groups. The bonds may be formed between side chains of amino acids, non-amino acid components or a combination of the two.

Peptides of the present invention may be converted into pharmaceutical salts by reacting with inorganic acids including hydrochloric acid, sulphuric acid, hydrobromic acid, phosphoric acid, etc., or organic acids including formic acid, acetic acid, propionic acid, glycolic acid, lactic acid, pyruvic acid, oxalic acid, succinic acid, malic acid, tartaric acid, citric acid, benzoic acid, salicylic acid, benzenesulphonic acid, and tolunesulphonic acids.

The peptides of the invention may be prepared as N-terminal or C-terminal fusion proteins. The fusion proteins may be prepared by fusing, through recombinant techniques or by chemical crosslinking, the N-terminal or C-terminal of the peptide, and the sequence of a selected protein or selectable marker with a desired biological function. The resultant fusion proteins contain the peptide fused to the selected protein or marker protein as described herein. Examples of proteins which may be used to prepare fusion proteins include immunoglobulins, glutathione-S-transferase, hemagglutinin, and truncated myc.

The peptides of the invention may be used to prepare monoclonal or polyclonal antibodies. Conventional methods can be used to prepare the antibodies. As to the details relating to the preparation of monoclonal antibodies reference can be made to Goding, J. W., Monoclonal Antibodies: Principles and Practice, 2nd Ed., Academic Press, London, 1986. As discussed below, the antibodies may be used to identify proteins that bind HA.

The peptides and antibodies specific for the peptides of the invention may be labelled using conventional methods with various enzymes, fluorescent materials, luminescent materials and radioactive material. Suitable enzymes, fluorescent materials, luminescent materials, and radioactive material are well known to the skilled artisan. Labelled antibodies specific for the peptides of the invention may be used to screen for proteins with HA binding sites as discussed in further detail below.

Preparation of the Peptides

The peptides of the invention may be prepared by chemical synthesis using techniques well known in the chemistry of proteins such as solid phase synthesis (Merrifield, *J. Am. Chem. Assoc.* 85:2149–2154 (1964)) or synthesis in homogenous solution (Houbenweyl, Methods of Organic Chemistry, ed. E. Wansch, Vol. 15 I and II, Thieme, Stuttgart (1987)).

The peptides of the invention may also be produced by recombinant DNA technology. To prepare the peptides of the invention by recombinant DNA techniques, a DNA sequence encoding the HA-binding peptide must be prepared. Consequently, the present invention also provides purified and isolated nucleic acid having a nucleotide sequence encoding a HA-binding peptide comprising an amino acid sequence of the formula I, II or III wherein the substituents are described above. In one embodiment, the DNA sequence encoding a HA-binding peptide of the formula I comprises a nucleotide sequence of ACC ATG ACC CGT CCG CAC TTC CAC AAA CGT CAG CTG GTT CTG TCT (SEQ.ID.NO.:5) or ACS ATG ACS CGS CCS CAC TTC CAC AAG CGS CAG CTS GTS CTS WSS wherein S is C or G and W is A or T (SEQ.ID.NO.: 6). In a second embodiment, the DNA sequence encoding a HA-binding peptide of the formula II comprises a nucleotide sequence of TCT ACC ATG ATG TCT CGT TCT CAC AAA ACC CGT TCT TGT CAC CAC (SEQ.ID.NO.: 7) or WSS ACS ATG ATG WSS CGS WSS CAC AAG ACS CGS WSS TGC CAC CAC wherein S is C or G and W is A or T (SEQ.ID.NO.:8). In a third embodiment, the DNA sequence encoding a HA-binding peptide of the formula III comprises a nucleotide sequence: TCT ACC ATG ATG TCT CGT TCT CAC AAA ACC CGT TCT CAC CAC (SEQ.ID.NO.:9) or WSS ACS ATG ATG WSS CGS WSS CAC AAG ACS CGS WSS CAC CAC wherein S is C or G and W is A or T (SEQ.ID.NO.:10) or TCT ACC ATG ATG TCT CGT TCT CAC AAA ACC CGT TCT CAC CAC GTG (SEQ.ID.NO.:11) or WSS ACS ATG ATG WSS CGS WSS CAC AAG ACS CGS WSS CAC CAC GTC wherein S is C or G and W is A or T (SEQ.ID.NO.:12).

The present invention also provides an expression vector comprising a DNA molecule encoding a HA-binding peptide adapted for transfection or transformation of a host cell. The nucleic acid molecules of the present invention may be incorporated in a known manner into an appropriate expression vector which ensures expression of the protein. Possible expression vectors include but are not limited to cosmids, plasmids, or modified viruses (e.g. replication defective retroviruses, adenoviruses and adeno-associated viruses). The vector should be compatible with the host cell used. The expression vectors are "suitable for transformation of a host cell", which means that the expression vectors contain a nucleic acid molecule of the invention and regulatory sequences selected on the basis of the host cells to be used for expression, which is operatively linked to the nucleic acid molecule. Operatively linked is intended to mean that the nucleic acid is linked to regulatory sequences in a manner which allows expression of the nucleic acid.

The invention therefore contemplates a recombinant expression vector containing a nucleic acid molecule of the invention, or a fragment thereof, and the necessary regulatory sequences for the transcription and translation of the inserted protein-sequence.

Suitable regulatory sequences may be derived from a variety of sources, including bacterial, fungal, viral, mammalian, or insect genes (For example, see the regulatory sequences described in Goeddel, Gene Expression Technology: Methods in Enzymology 185, Academic Press, San Diego, Calif. 1990). Selection of appropriate regulatory sequences is dependent on the host cell chosen as discussed below, and may be readily accomplished by one of ordinary skill in the art. Examples of such regulatory sequences include: a transcriptional promoter and enhancer or RNA polymerase binding sequence, a ribosomal binding sequence, including a translation initiation signal. Additionally, depending on the host cell chosen and the vector employed, other sequences, such as an origin of replication, additional DNA restriction sites, enhancers, and sequences conferring inducibility of transcription may be incorporated into the expression vector. It will also be appreciated that the necessary regulatory sequences may be supplied by the native A and B chains and/or its flanking regions.

The recombinant expression vectors of the invention may also contain a selectable marker gene which facilitates the selection of host cells transformed or transfected with a recombinant molecule of the invention. Examples of selectable marker genes are genes encoding a protein such as G418 and hygromycin which confer resistance to certain drugs, β-galactosidase, chloramphenicol acetyltransferase, firefly luciferase, or an immunoglobulin or portion thereof such as the Fc portion of an immunoglobulin preferably IgG. Transcription of the selectable marker gene is monitored by changes in the concentration of the selectable marker protein such as β-galactosidase, chloramphenicol acetyltransferase, or firefly luciferase. If the selectable marker gene encodes a protein conferring antibiotic resistance such as neomycin resistance transformant cells can be selected with G418. Cells that have incorporated the selectable marker gene will survive, while the other cells die. This makes it possible to visualize and assay for expression of recombinant expression vectors of the invention and in particular to determine the effect of a mutation on expression and phenotype. It will be appreciated that selectable markers can be introduced on a separate vector from the nucleic acid of interest.

Recombinant expression vectors can be introduced into host cells to produce a transformant host cell. The term "transformant host cell" is intended to include prokaryotic and eukaryotic cells which have been transformed or transfected with a recombinant expression vector of the invention. The terms "transformed with", "transfected with", "transformation" and "transfection" are intended to encompass introduction of nucleic acid (e.g. a vector) into a cell by one of many possible techniques known in the art. Prokaryotic cells can be transformed with nucleic acid by, for example, electroporation or calcium-chloride mediated transformation. Nucleic acid can be introduced into mammalian cells via conventional techniques such as calcium phosphate or calcium chloride co-precipitation, DEAE-dextran mediated transfection, lipofectin, electroporation or microinjection. Suitable methods for transforming and transfecting host cells can be found in Sambrook et al. (Molecular Cloning: A Laboratory Manual, 2nd Edition, Cold Spring Harbor Laboratory press (1989)), and other laboratory textbooks.

Suitable host cells include a wide variety of prokaryotic and eukaryotic host cells. For example, the proteins of the invention may be expressed in bacterial cells such as *E. coli*, insect cells (using baculovirus), yeast cells or mammalian cells. Other suitable host cells can be found in Goeddel, Gene Expression Technology: Methods in Enzymology 185, Academic Press, San Diego, Calif. (1991).

More particularly, bacterial host cells suitable for carrying out the present invention include *E. coli, B. subtilis, Salmonella typhimurium*, and various species within the genus' Pseudomonas, Streptomyces, and Staphylococcus, as well as many other bacterial species well known to one of ordinary skill in the art. Suitable bacterial expression vectors preferably comprise a promoter which functions in the host cell, one or more selectable phenotypic markers, and a bacterial origin of replication. Representative promoters include the β-lactamase (penicillinase) and lactose promoter system (see Chang et al., *Nature* 275:615 (1978)), the trp promoter (Nichols and Yanofsky, *Meth. in Enzymology* 101:155, 1983) and the tac promoter (Russell et al., *Gene* 20: 231, 1982). Representative selectable markers include various antibiotic resistance markers such as the kanamycin or ampicillin resistance genes. Suitable expression vectors include but are not limited to bacteriophages such as lambda derivatives or plasmids such as pBR322 (see Bolivar et al., *Gene* 2:9S, (1977)), the pUC plasmids pUC18, pUC19, pUC118, pUC119 (see Messing, Meth in Enzymology 101:20–77, 1983 and Vieira and Messing, *Gene* 19:259–268 (1982)), and pNH8A, pNH16a, pNH18a, and Bluescript M13 (Stratagene, La Jolla, Calif.). Typical fusion expression vectors which may be used are discussed above, e.g. pGEX (Amrad Corp., Melbourne, Australia), pMAL (New England Biolabs, Beverly, Mass.) and pRIT5 (Pharmacia, Piscataway, N.J.). Examples of inducible non-fusion expression vectors include pTrc (Amann et al., *Gene* 69:301–315 (1988)) and pET 11d (Studier et al., Gene Expression Technology: Methods in Enzymology 185, Academic Press, San Diego, Calif., 60–89 (1990)).

Yeast and fungi host cells suitable for carrying out the present invention include, but are not limited to *Saccharomyces cerivisae*, the genera Pichia or Kluyveromyces and various species of the genus Aspergillus. Examples of vectors for expression in yeast *S. cerivisae* include pYepSec1 (Baldari. et al., *Embo J*. 6:229–234 (1987)), pMFa (Kurjan and Herskowitz, *Cell* 30:933–943 (1982)), pJRY88 (Schultz et al., *Gene* 54:113–123 (1987)), and pYES2 (Invitrogen Corporation, San Diego, Calif.). Protocols for the transformation of yeast and fungi are well known to those of ordinary skill in the art.(see Hinnen et al., *Proc. Natl. Acad. Sci. USA* 75:1929 (1978); Itoh et al.,*J. Bacteriology* 153:163 (1983), and Cullen et al. (*Bio/Technology* 5:369 (1987)).

Mammalian cells suitable for carrying out the present invention include, among others: COS (e.g., ATCC No. CRL 1650 or 1651), BHK (e.g. ATCC No. CRL 6281), CHO (ATCC No. CCL 61), HeLa (e.g., ATCC No. CCL 2), 293 (ATCC No. 1573) and NS-1 cells. Suitable expression vectors for directing expression in mammalian cells generally include a promoter (e.g., derived from viral material such as polyoma, Adenovirus 2, cytomegalovirus and Simian Virus 40), as well as other transcriptional and translational control sequences. Examples of mammalian expression vectors include pCDM8 (Seed, B., *Nature* 329:840 (1987)) and pMT2PC (Kaufman et al., *EMBO J*. 6:187–195 (1987)).

Given the teachings provided herein, promoters, terminators, and methods for introducing expression vectors of an appropriate type into plant, avian, and insect cells may also be readily accomplished. For example, within one embodiment, the proteins of the invention may be expressed from plant cells (see Sinkar et al., *J. Biosci* (Bangalore) 11:47–58 (1987), which reviews the use of *Agrobacterium rhizogenes* vectors; see also Zambryski et al., Genetic Engineering, Principles and Methods, Hollaender and Setlow (eds.), Vol. VI, pp. 253–278, Plenum Press, New York (1984), which describes the use of expression vectors for plant cells, including, among others, pAS2022, pAS2023, and pAS2034).

Insect cells suitable for carrying out the present invention include cells and cell lines from Bombyx or Spodotera species. Baculovirus vectors available for expression of proteins in cultured insect cells (SF 9 cells) include the pAc series (Smith et al., *Mol. Cell Biol*. 3:2156–2165 (1983)) and the pVL series (Lucklow, V. A., and Summers, M. D., *Virology* 170:31–39 (1989)). Some baculovirus-insect cell expression systems suitable for expression of the recombinant proteins of the invention are described in PCT/US/02442.

The recombinant expression vectors containing the nucleotide sequences encoding the HA-binding peptides may also contain genes which encode a fusion moiety which provides increased expression of the recombinant peptide; increased solubility of the recombinant peptide; and aid in the purification of the target recombinant peptide by acting as a ligand in affinity purification. For example, a proteolytic cleavage site may be added to the target recombinant protein to allow separation of the recombinant protein from the fusion moiety subsequent to purification of the fusion protein. Typical fusion expression vectors include pGEX (Amrad Corp., Melbourne, Australia), pMAL (New England Biolabs, Beverly, Mass.) and pRIT5 (Pharmacia, Piscataway, N.J.) which fuse glutathione S-transferase (GST), maltose E binding protein, or protein A, respectively, to the recombinant protein. By way of illustration, the DNA sequence encoding an enhanced affinity HA binding peptide may be cloned into a pGEX-type plasmid for co-expression with a 26 kD protein glutathione-S-transferase (GST): pGEX-2T, pGEX-2TK, pGEX-3X, pGEX-1T, pGEX-4T, pGEX-5X. Said plasmids are transformed into *Escherichia coli* HB101 cells, and positive clones can then be selected by standard hybridization techniques identifying GST-HA binding peptide fusion protein. Colonies with the pGEX-2T plasmids containing DNA encoding an enhanced affinity HA binding peptide may be grown in 5 mL of LB/amp medium at 37° C. for overnight. Isopropylthio-D-galactoside is added to the culture to a final concentration of 0.1 mM to induce the biosynthesis of the fusion protein. The cultures are grown for 90 min post induction and the cells are harvested by centrifugation and lysed in 1 mL of 50 mM Tris-HCl, pH 8.0, containing 2 M urea and 1% Triton X-100. Cells can then be further disrupted by sonication and centrifuged at 15,000×g for 20 min to separate soluble from insoluble fractions. The supernatant containing the GST-HA binding peptide fusion protein is then used for extraction of the fusion protein by standard procedures (GST Purification Module: Pharmacia Cat. #27-4570-01, -02). Subsequently, the fusion protein may be treated with an enzyme to release the enhanced affinity HA-binding peptide (thrombin for pGEX-2T, pGEX-2TK, pGEX-1T, pGEX-4T; factor Xa for pGEX-3X and pGEX-5X).

Another aspect of the invention provides a nucleotide sequence which hybridizes under high stringency conditions to a nucleotide sequence encoding a HA-binding peptide. Appropriate stringency conditions which promote DNA hybridization are known to those skilled in the art, or can be found in Current Protocols in Molecular Biology, John Wiley & Sons, N.Y. (1989), 6.3.1 6.3.6. For example, 6.0×sodium chloride/sodium citrate (SSC) at about 45° C., followed by a wash of 2.0×SSC at 50° C. may be employed. The stringency may be selected based on the conditions used in the wash step. By way of example, the salt concentration in the wash step can be selected from a high stringency of about 0.2×SSC at 50° C. In addition, the temperature in the wash step can be at high stringency conditions, at about 65° C.

Isolation of HA-Binding Peptides

HA-binding peptides may be isolated by assaying a sample for peptides that bind to HA. Any assay system or testing method that detects protein-protein interactions may be used including co-immunoprecipitation, crosslinking and co-purification through gradients or chromatographic columns may be used. Biological samples and commercially available libraries may be tested for HA-binding peptides. For example, labelled HA may be used to probe phage display libraries as is described in greater detail in Example 1. In addition, antibodies prepared to the peptides of the invention may be used to isolate other peptides with HA binding affinity. For example, labelled antibodies may be used to probe phage display libraries or biological samples.

Additionally, a DNA sequence encoding a HA protein may be used to probe biological samples or libraries for nucleic acids that encode HA-binding proteins.

Applications of the Peptides

The inventor has demonstrated that the HA binding peptides of the present invention are able to influence and inhibit cell motility and locomotion in vivo and in vitro. Consequently, the present invention includes the use of one or more HA-binding peptides of the invention to modulate cell locomotion. Accordingly, the present invention provides a method of modulating cell locomotion comprising administering an effective amount of a HA binding peptide or a nucleic acid molecule encoding a HA binding peptide of the invention to a cell or animal in need thereof.

The term "effective amount" as used herein means an amount effective, at dosages and for periods of time necessary to achieve desired results.

More specifically, the peptides of the invention may be used in the prophylaxis or treatment of pathological conditions involving cell locomotion such as cancer, inflammatory and autoimmune disorders, and fibrotic disorders associated with tissue trauma and its recovery in a mammal.

In one embodiment, the HA binding peptides of the present invention are useful for prevention of fibrosis of adult human tissues thereby eliminating clinical pathologies resulting from the malfunction of tissues due to keloids, hypertrophic scars, anatomonic strictures, intra-abdominal adhesions, cirrhosis of the liver, neurological deficits following spinal cord injury, valvular heart diseases, burn-injured joints as well as failure of anastomosis and adhesions following surgery. Accordingly, the present invention provides a method of preventing or inhibiting tissue fibrosis comprising administering an effective amount of a HA binding peptide of the invention to an animal in need thereof.

Pretreatment of skin wounds with enhanced affinity HA binding peptides have resulted in significant reduction in fibroblast activity and deposition of collagen at the wound site thereby preventing wound contraction and tissue fibrosis. As mentioned above, fibrosis of adult human tissues is a serious clinical pathology which can result in malfunction of tissues due to keloids, hypertrophic scars, anatomonic strictures, intra-abdominal adhesions, cirrhosis of the liver, neurological deficits following spinal cord injury, valvular heart diseases, burn-injured joints as well as failure of anastomosis and adhesions following surgery. The application of enhanced affinity HA binding peptides therapeutically to skin injuries can reduce or eliminate the adversities associated with tissue fibrosis during wound healing and these peptides possess important clinical utilities, both for therapeutic and for aesthetic purposes. Notable examples of surgical procedures which may benefit from the treatment with RHAMM-peptides include coronary balloon angioplasty (prevention of restenosis), small intestinal resections (e.g. in Crohn's Disease), surgery of the renal system (e.g. ureteral connection in renal transplants), and vascular surgery. Similarly, the application of RHAMM-peptides in plastic and cosmetic surgery can minimize the aesthetic consequences of hypertrophic scars and skin disfiguration.

Accordingly, the present invention provides a method of preventing or reducing tissue scarring comprising administering an effective amount of a HA binding peptide or a nucleic acid molecule encoding a HA binding peptide of the invention to an animal in need thereof.

In a further embodiment, the peptides of the invention are useful in treating cancers that are associated with the activation of the ras-oncogene including cancer of the lung, gastrointestinal, breast, bladder, skin cancer (melanoma and non-melanoma), brain, cervix, and leukemia. Accordingly, the present invention provides a method of preventing or treating cancer comprising administering an effective amount of a HA binding peptide or a nucleic acid molecule encoding a HA binding peptide of the invention to an animal in need thereof.

Locomotion and motility of tumour cells are fundamental to their ability to invade other tissues and metastasize and prior studies have shown that highly metastatic cancer cells locomote more rapidly than slow- or non-metastatic cells (Mohler, J. L. et al., *J. Urol.* 138:168–170, 1987; Raz, A. et al., *Cancer Metas. Rev.* 6: 3021, 1987; Hosaka, S. et al., *Gann* 69: 273–276, 1978). Furthermore, enhanced affinity HA binding peptides of this invention may also elicit beneficial impact on activation of the ras oncogene and carcinogenesis. Initial studies have shown that administration of enhanced affinity HA binding peptides terminated replication of malignant cells at the $G_2/M$ phase of the cell cycle and induced apoptosis.

The ability of the present enhanced affinity HA binding peptides to inhibit the motility ras-transformed cells implicates their effectiveness in preventing tumour metastasis and their utility as cancer chemotherapeutic agents. Accordingly, the present invention provides a method of preventing or reducing tumour metastasis comprising administering an effective amount of a HA binding peptide or a nucleic acid molecule encoding a HA binding peptide of the invention to an animal in need thereof.

The peptides and nucleic acid molecules of the invention may be formulated into pharmaceutical compositions for adminstration to subjects in a biologically compatible form suitable for administration. By biologically compatible form suitable for administration is meant a form of the substance to be administered in which any toxic effects are outweighed by the therapeutic effects. The substances may be administered to living organisms including humans, and animals in a therapeutically effective amount. Administration of an effective amount of the pharmaceutical compositions of the present invention is defined as an amount effective, at dosages and for periods of time necessary to achieve the desired result. For example, a therapeutically active amount of a substance may vary according to factors such as the disease state, age, sex, and weight of the individual, and the ability of peptide to elicit a desired response in the individual. Dosage regime may be adjusted to provide the optimum therapeutic response. For example, several divided doses may be administered daily or the dose may be proportionally reduced as indicated by the exigencies of the therapeutic situation.

The active substance may be administered in a convenient manner such as by topical or transdermal application, injection (subcutaneous, intravenous, etc.), oral administration, inhalation, or rectal administration. Depending on the route of administration, the active substance may be coated in a material to protect the compound from the action of enzymes, acids and other natural conditions which may inactivate the compound.

Several modes of administration are available when using a composition containing a nucleic acid molecule encoding a HA binding peptide of the invention. Recombinant molecules comprising an nucleic acid sequence encoding a HA binding protein (as described above), or fragment thereof, may be directly introduced into cells or tissues in vivo using delivery vehicles such as retroviral vectors, adenoviral vectors and DNA virus vectors. They may also be introduced into cells in vivo using physical techniques such as microinjection and electroporation or chemical methods such as coprecipitation and incorporation of DNA into liposomes. Recombinant molecules may also be delivered in the form of an aerosol or by lavage. The nucleic acid molecules of the invention may also be applied extracellularly such as by direct injection into cells.

The compositions described herein can be prepared by per se known methods for the preparation of pharmaceutically acceptable compositions which can be administered to subjects, such that an effective quantity of the active substance is combined in a mixture with a pharmaceutically acceptable vehicle. Suitable vehicles are described, for example, in Remington's Pharmaceutical Sciences (Remington's Pharmaceutical Sciences, Mack Publishing Company, Easton, Pa., USA 1985). On this basis, the compositions include, albeit not exclusively, solutions of the substances in association with one or more pharmaceutically acceptable vehicles or diluents, and contained in buffered solutions with a suitable pH and iso-osmotic with the physiological fluids.

Compositions for injection include, albeit not exclusively, the peptides or nucleic acids in association with one or more pharmaceutically acceptable vehicles or diluents, and contained in buffered solutions with a suitable pH and iso-osmotic with the physiological fluids. Any pharmaceutically suitable diluent can be used in the composition for injections: distilled water, physiological or a salt solution, and/or a buffer solution. The composition for injections may be prepared by conventional volume-weight procedures. A certain amount of the peptide is diluted to the necessary volume with a diluent or solvent. The solution is then filtered through sterilized filters, bottled or ampouled. The resultant solution is a stable transparent liquid, and does not contain any chemical or other impurities.

Solid form preparations for oral administration can be made in the form of tablets, powders, or capsules. It may contain a medium for the active substance and other additives, including dyes, aromas, etc.

The compositions and treatments are indicated as therapeutic agents or treatments either alone or in conjunction with other therapeutic agents or other forms of treatment.

EXAMPLES

Example 1

Isolation of HA-Binding Peptides Using Phage Display Technology

A 15-mer phage display library was obtained from Chiron Inc. (CA). Hyaluronan (HA) was biotinylated and mixed with streptavidin-sepharose (Sigma) and washed. The Biotinylated HA was incubated with the phage library, then recovered with streptavidin-sepharose. The phage biotinylated HA-streptavidin-sepharose mixture was washed 4 times with phosphate buffered saline (PBS) and recovered phage were plated on a bacteria lawn in petri dishes. Clones were isolated and assessed for their ability to bind to HA. For the first screen, a total 75 clones were obtained after 4 cycles of screening. To assess the specificity of binding of these clones to HA, two approaches were taken. In the first, the ability of the clones to bind to biotin-sepharose or to streptavidin-sepharose were assessed. Clones were recovered from the bacteria lawn and mixed with biotin-sepharose and streptavidin-sepharose. Sepharose beads were washed 4 times with PBS and plated onto a bacteria lawn. In the second assay, clones were mixed with excess (100 ug/mL) HA (mean molecular weight: 700,000 daltons (Hyal, Ontario, Canada) together with biotinylated HA. After mixing the biotinylated HA was recovered with streptavidin-sepharose, washed as above and plated onto a bacteria lawn. Clones were sequenced in an automatic sequencer. A schematic diagram illustrating the isolation of enhanced affinity hyaluronan binding peptides from the 15-mer phage display library is shown in FIG. 1.

Assessment of HA-Binding Properties of Peptides

Enhanced affinity HA binding peptides mimicking sequences obtained from the phage display library and scrambled peptides prepared from these sequences were tested for their HA binding properties. HA was derivatized to NUNC ELISA plates and biotinylated peptides were added to the plates and incubated for 2 h at room temperature. Plates were washed 4 times with PBS and then incubated with streptavidin-peroxidase for 1 h, washed, developed with hydrogen peroxide and their optical densities were determined. Controls were conducted using BSA-coated ELISA wells.

Enhanced affinity binding peptides were determined and found to possess the two following sequences. The first sequence (45 clones) encoded STMMSRSHKTRSHHV while the second sequence (30 clones) encoded TMTRPHFHKRQLVLS. The inventor has shown that a peptide of the first sequence that has the C-terminal valine removed (i.e., STMMSRSHKTRSHH) or has a cysteine residue at position 13 inserted and the C-terminal valine deleted (i.e., STMMSRSHKTRSCHH) also can bind to HA.

The peptide sequences of the present invention are different from the HA binding motif disclosed by Yang et al. and represented by the generic formula $B^1$-$A_n$-$B^2$ (wherein $B^1$ and $B^2$ are the same or different basic amino acid residues and $A_n$ is a peptide sequence containing seven or eight amino acid residues which are the same or different and are neutral or basic amino acids (Yang, B. et al., *J. Biol. Chem.* 268: 8617–8623, 1993)). In particular, Yang et al. state that when $B^2$ is a histidine residue the HA-binding ability of the RHAMM peptides is abolished. Consequently, the peptides STMMSRSHKTRSHHV, STMMSRSHKTRSHH and STMMSRSHKTRSCHH would not be expected to bind HA according to the Yang et al. formula. In addition, the second sequence TMTRPHFHKRQLVLS does not contain a $B^1$-$A_n$-$B^2$ motif as n can not be a peptide sequence containing five amino acid residues. Yang et al. demonstrated a lost in binding activity if $A_n$ is less than seven or greater than eight amino acid residues. Therefore, the peptides of the present invention are distinct to those described in this reference based on the exclusion criteria clearly defined as critical by Yang et al. Moreover, the novel enhanced affinity hyaluronan binding peptides of the present invention exhibit higher HA binding affinity (nanomolar range) than the nonomeric and decameric peptides previously described.

Example 2
Effect of Enhanced Affinity HA-binding Peptide on Cell Locomotion In Vitro Cell Culture Ras-transformed 10T1/2 or parental 10T1/2 fibroblasts (Egan, S. E. et al., *Science* 238: 202–205, 1987; Hardwick, C. et al., *J. Biol. Chem.* 117: 1343–1350, 1992) were cultured in DMEM containing 10% fetal bovine serum (FBS) and maintained in 5% $CO_2$ humidified atmospheric condition. Every second passage, cells were maintained in 600 ug/mL G418 for one passage to select for maintenance of the mutant active ras-geneticin construct in cells. Cells were passaged at confluence and utilized under 20 passages. Macrophages were obtained from lung lavage 1 h after bleomycin insertion (Gelzleichter, T. R. et al., *Fund. Appl. Toxicol.* 30: 39–46, 1996) and used immediately in assays. Neutrophils were obtained from human blood as described and used immediately.

Immunofluorescence

Ras-transformed or parental 10T1/2 fibroblasts (Egan, S. E. et al., *Science* 238: 202–205, 1987) were subcultured onto fibronectin coated (20 ug/mL) glass coverslips and cultured for 24–48 h. The enhanced affinity hyaluronan binding peptide (shown in SEQ.ID.NO.:3) or scrambled peptides were added at 100 ng/mL to cultures and cells were fixed at 10 min, 20 min, 1 h and 2 h after the addition of peptides. Cultures were washed carefully in phosphate buffered saline (PBS) and then fixed in freshly prepared 3.5% paraformaldehyde for 20 min at 4° C. Fixed monolayers were washed in PBS and then incubated in 1.0 M glycine to reduce autofluorescence. Cultures were washed again and then incubated with anti-vinculin antibody (1:100, Pharmingen) for 2 h. Cultures were mounted and observed with an epifluorescence microscope (Zeiss).

For routine analysis of random locomotion, 10T1/2 fibroblasts or leukocytes were subcultured into culture flasks coated with 20 ug/mL fibronectin and maintained in DMEM plus 10% FBS for 24–48 h. The enhanced affinity hyaluronan binding peptide (shown in SEQ.ID.NO.:3) or scrambled peptides were incubated with the cultures at concentrations of 50 ng to 1 ug per mL. Concentrations of 50–100 ng/mL were found to be optimal for inhibiting cell motility. Cells were observed with Hoffman optics and the image analysis program automatically follows the outline of the cells. Filming was conducted for up to 24 h with images recorded every 20 min. A total of 100 cells were observed for each experimental condition.

For serum stimulation of cell motility, cells were plated onto fibronectin-coated culture dishes (30 ug/mL) and grown in 10% FBS to semi-confluence. Cells were then maintained in defined medium for 24 h. Medium was removed and replaced with medium containing 10% FBS and cell motility was monitored as above.

To assess the effects of enhanced affinity hyaluronan binding peptides and scrambled peptides on chemotaxis, a modified multi-well boyden chamber was utilized as described by Shi, Y. et al. (*J. Immunol. Methods* 164: 149–154, 1993).

Protein Tyrosine Phosphorylation

Cultures were grown to 70–80% confluence and were then serum-starved for 24 h. DMEM medium containing 10% FBS was added to cells in the presence or absence of the enhanced affinity hyaluronan binding peptide (shown in SEQ.ID.NO.:3) or scrambled peptides, and the cells were monitored for their motility for periods of up to 3 h. At the end of each filming period, cell monolayers were extracted with RIPA and 10 ug of protein was electrophoresed on SDS-PAGE. Separated protein was transferred to nitrocellulose blots and was then processed for protein tyrosine phosphorylation using an anti-phosphotyrosine antibody (Shi, Y. et al., *J. Cell. Biol.* 126: 575–588, 1994). An equal amount of sample was also electrophoresed on SDS-PAGE in an identical manner and was stained with Coomassie Blue to assess protein loading.

FAK Immunoprecipitation

Cultures were tested with peptides as described above then monolayers were extracted with RIPA buffer. The extract was microcentrifuged for 3 min. to remove particulate material. Anti-FAK antibody was incubated with the extract for 2 h then the antibody was captured using anti-mouse IgG-sepharose. The complex was washed 3 times then FAK was removed from the complex by boiling in SDS-PAGE loading buffer and electrophoresed in SDS-PAGE. Protein was then transferred to a nitrocellulose blot and the blot was stained for protein tyrosine phosphorylation using an anti-tyrosine antibody. Blots were then stripped and reincubated with the anti-FAK antibody and processed as above to detect loading of immunoprecipitated FAK.

Cell Proliferation

10T1/2 fibroblasts were grown to semi-confluence and were incubated with enhanced affinity hyaluronan binding peptide (shown in SEQ.ID.NO.:3) at a concentration of 100 ug/mL for 48 h. The cells were then trypsinized in 0.12% trypsin and counted using a hematocytometer. Released cells were stained with trypan blue and only viable cells were counted.

Apoptosis

Ras-transformed 10T1/2 fibroblasts were grown to sub-confluence and were incubated with enhanced affinity hyaluronan binding peptide (shown in SEQ.ID.NO.:3) at a concentration of 100 ug/mL for 48 h. The cells were then stained with Hoechst dye using standard procedures and the percentage of apoptotic cells were determined by detection of positive stain in the nucleus of randomly selected cells.

Results on Cell Locomotion and Protein Tyrosine Phosphorylation

HA/RHAMM interactions have been shown to control focal adhesion turnover during cell locomotion and levels of protein tyrosine phosphorylation. The effects of enhanced affinity hyaluronan binding peptides on focal adhesion formation and protein tyrosine phosphorylation were examined.

Enhanced affinity hyaluronan binding peptides were shown to strongly inhibit fibroblast random motility (TABLES II and III). The formation of focal adhesions was observed when the cells were plated on fibronectin substrata (FIGS. 2A–F). Focal adhesion assembly was enhanced by 20 min following the addition of enhanced affinity hyaluronan binding peptides and was maintained at high levels for several hours. This effect appeared to be due to the ability of the peptides to sequester HA as treatment of cells with Streptomyces with hyaluronidase produced a similar effect on focal adhesion formation (FIG. 2G).

Figure 3I:
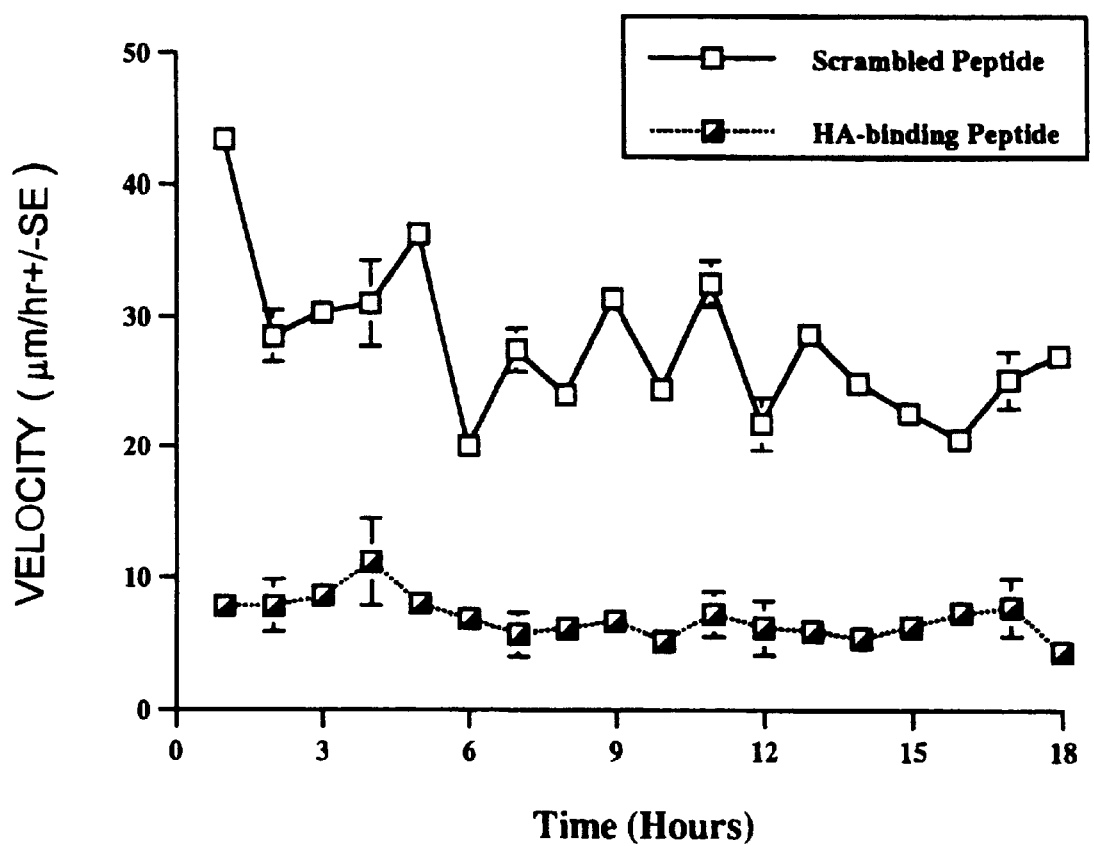

Serum-starved cells exhibited slowed cell motility, and re-introduction of serum enhanced cell locomotion (FIGS. 3F–H). When cell motility was monitored over short time periods, regular fluctuations in the rate of locomotion was apparent. Such fluctuations in motility coincided with cycles of protein tyrosine phosphorylation/dephosphorylation of various proteins. The rate of protein tyrosine phosphorylation was reciprocally correlated with motility rate. Addition of enhanced affinity hyaluronan binding peptides inhibited cycling of protein tyrosine dephosphorylation (most notably of proteins of MW 125, 85 and 70 kD) and inhibited fluctuations in cell motility (FIGS. 3A–H). The duration of inhibitory effect was over 18 h following administration (FIG. 3I).

Example 3
Effect of Enhanced Affinity HA-binding Peptide on Wound Repair In Vivo Punch Biopsy Model Response to injury of skin involves extensive extracellular remodelling initiated by infiltration of fibroblasts and leucocytes. The adult skin healing process involves an acute and transient increase in HA production followed by deposition of extracellular matrix glycoproteins such as collagen. Healing is achieved with extensive leucocyte infiltration and the consequent release of growth factors that attract and stimulate and enhance proliferation of fibroblasts. This fibroproliferative response is accompanied by wound contraction and fibrosis due to the presence of myobroblasts and to the enhanced production of collagen.

The early deposition of HA following skin injury has been shown to regulate leucocyte chemotaxis and function. Neutral hyaluronidases are released by macrophages and the production of oligosaccharides and from polymeric HA may in turn stimulate the release of growth factors such as TGFβ-1 that alter macrophage and fibroblast function. However, as mentioned above, the effects of HA is governed by the level of accumulation wherein high HA concentrations paradoxically inhibits fibroblast migration, angiogenesis, and the ability of fibroblasts to contract collagen gels.

As also aforementioned, the major biological responses to HA in tissue remodelling are mediated through at least two HA receptors, CD44 and RHAMM. CD44 has been implicated in to be involved in promoting the motility and proliferation within epidermal structures and to be required for the efficient repair of skin. Similarly, RHAMM has been shown to be overexpressed in activated white cells and fibroblasts migrating in response to growth factors.

In order to further delineate the significance of HA/RHAMM interaction in the wound healing process and to demonstrate the clinical utility of enhanced affinity HA-binding peptides, a rat punch biopsy model of skin repair was used to investigate the expression of RHAMM and the in vivo effects of the HA binding peptides of the present invention with respect to the severity of fibrotic response following tissue trauma. Collagen was used as a vehicle to stimulate inflammation and fibrosis as rat skin normally exhibits minimal fibrosis.

Three-month-old female Fischer rats were anesthesized and subjected to 47 mm full thickness punch biopsies. Wounds were filled with a sterile solution of 1% collagen type 1 gel containing either PBS alone, HA binding peptide (shown in SEQ.ID.NO.:3) (20 mg/mL) or scrambled peptide (20 mg/mL) that contained the same amino acids as the HA binding peptide but in a random order. 100 uL of the collagen solution was applied to the punch biopsy wound and allowed to gel over 20 min. The wounds were then covered with a protective plastic shield that was sewn into the skin. Wounds were recovered from euthenized rats with a 9 mm punch biopsy.

Western Analyses

Recovered punch biopsies were extracted with RIPA buffer and total protein was determined with a Biorad protein assay. Protein (50 ug) was loaded onto each lane and proteins were separated by electrophoresis on SDS-PAGE. Separated proteins were transferred to a nitrocellulose blot and the blot was processed for reactivity to anti-RHAMM antisera or anti-CD44 antibody (Dillon, P. W. et al., *J. Surg. Res.* 57:170–173, 1994).

Isolation of mRNA and RT-PCR

Messenger RNA was isolated by Micro-FastTrack Kit (Invitrogen, San Diego, Calif.). The quality of RNA samples was confirmed by denaturing gel electrophoresis. Reverse transcription was performed by using First Strand cDNA Synthesis kit (Clontech, Polo Alco, Calif.). Briefly, 0.2 ug of mRNA was used to generate cDNA using oligo(dT) 18 primer. Samples containing 0.2 ug of mRNA per time point was heat-denatured in DEPC-treated water for 2 min at 70° C. and incubated at 42° C. for 1 h in a total volume of 20 uL of 20 pmol primers, 0.5 mM of each dNTP, 1 unit/uL of RNase inhibitor and 200 units/ug RNA of MMLV. The reaction was stopped by heating at 94° C. for 5 min and to destroy any DNase activity. The reaction mixture was diluted to a final volume of 100 uL and aliquots were stored at −80° C. until further use.

To distinguish between amplication of genomic DNA and complementary DNA, the primer pairs were designed to enclose at least one intron on the genomic sequences of RHAMM and beta-actin. The primers were synthesized by GIBCO and the sequences of the primers were as follows: Beta-actin A: 5' GTA ACC AAC TGG GAC GAT AT 3' (1554–1574) SEQ.ID.NO.:13; B: GAT CTT GAT CTT CAT GGT GCT 3' (2991–2841) SEQ.ID.NO.:14. RHAMM sense: 5' GGG TTA GTT ATG TTG GTT GGT 3' (SEQ.ID.NO.:15) (10–31 (Entwistle, J. et al., *J. Cell. Biochem.* 61: 569–577, 1996)), and antisense: 5' CTG AAG ATG AGC AGA CAG TTC (426–406) SEQ.ID.NO.:16. CD44 sense: 5' AAT GGC CGC TAC AGT ATC TCC AGG ACT GAA (263–266) SEQ.ID.NO.:17, CD44 antisense: 5' GTT GAT CAC CAG CTT CTT CTT CTG CCC ACA (1451–1421 (Gunthert, U. et al., *Cell* 65: 13–24,1991)) SEQ.ID.NO.:18. Collagen type I alpha 2 sense: 5' CCC ACG TAG GTG TCC TAA AGT SEQ.ID.NO.:19, and collagen type I alpha 2 antisense: 5' CCG TGG TGC TAA AAT AAT AAA SEQ.ID.NO.:20. Collagen type III sense: 5° CGA GGT AAC AGA GGT GAA AGA SEQ.ID.NO.:21, and collagen type III antisense: 5' AAC CCA GTA TTC TCC GCT CTT (Power, W. J. et al., *Curr. Eye Res.* 14: 879–886, 1995) SEQ.ID.NO.:22. The PCR amplification of cDNA was carried out by using Taq polymerase. Briefly, an aliquot of cDNA was added to a 100 uL reaction mixture containing 0.2 uM primers and 2.5 units of Taq polymerase. Amplification was performed for 30 cycles at 94° C. for 1 min of denaturation, 60° C. for 1 min of annealing and at 72° C. for 2 min of extension. The PCR products were electrophoresed in a 1% agarose gel and transferred to nylon transfer membranes (Amersham) and checked by Southern blot using an inter-nest probe.

Immunocytochemistry

Punch biopsies collected using an 11 mm punch were fixed in freshly prepared 3.5% paraformaldehyde and processed for paraffin sections. Sections of thickness of 15 um were obtained and deparaffinized in a series of alcohol. Sections were stained for RHAMM (Gunthert, U. et al., *Cell* 65: 13–24, 1991; Power, W. J. et al., *Curr. Eye Res.* 14: 879–886, 1995), ED-1 (Chandler, D. B. et al., *Am. J. Pathol.* 112: 170–177, 1983) and mac-3 (Pharmingen) using either anti-rabbit or anti-mouse IgG conjugated with horseradish peroxidase. Sections were developed as described in Gunthert and Power as described above.

Detection of HA

HA was detected using biotinylated aggrecan in either an ELISA or by histochemical staining (Hendin, B. N. et al., *Am. J. Card. Pathol.* 3: 209–215, 1990). Aggrecan was purified from calf's noses and biotinylated.

Enzyme Assays

To determine the specificity of biotinylated aggrecan for HA, tissues sections were first exposed to 0.1 TRU of Streptomyces hyaluronidase (Sigma) for 3 h. Sections were washed then incubated with biotinylated aggrecan as described above. To assess the effect of hyaluronidase on focal contraction formation of ras-transformed cells, varying concentrations of the enzyme were added to adherent cells for 1 h in buffer. Cells were then washed, fixed and processed for vinculin staining.

To quantify leucocytes present within wounds, tissue biopsies were extracted with RIPA buffer then processed for detection of glucosaminidase (Podhajsky, R. J. et al., *Exp. Neurol.* 143: 153–161, 1997; Gelzleichter, T. R. et al., *Fund. Appl. Toxicol.* 30: 39–46, 1996).

Staining disappeared when tissue sections were pretreated with Streptomyces hyaluronidase indicating that the biotinylated aggrecan used to detect HA was specific for this glycosaminoglycan.

Control Wound Repair Results

Western analysis and RT-PCR analysis of mRNA extracted from the wound site showed that RHAMM and CD44 expression was significantly increased after injury. As shown in FIGS. 4, 5A–D, 6A–B and 7A–B, CD44 and RHAMM expression was low in uninjured adult skin which increased after injury. This is confirmed by immunohistochemical data showing the virtual absence of RHAMM in uninjured skin.

Several RHAMM isoforms with molecular weight ranging from 60–80 kDa were detected by Western analysis and densitometry analysis showed that these isoforms increased above control levels by 24 h following injury. Histochemical analysis revealed that RHAMM expression was strongly upregulated in keratinocytes which was maintained at high levels for two weeks (FIGS. 5A–D and 17). At 24 h, RHAMM staining appeared to be at the cell surface and was localized primarily within the suprabasal epidermal layer. By 72 h, the entire epidermal layer was positive for RHAMM and staining then appeared to be primarily intracellular. RHAMM expression in infiltrated fibroblasts also showed marked increases in RHAMM expression and was observed to a lesser extent in infiltrated white blood cells. At 2 weeks after injury, RHAMM levels had diminished in both the dermal and epidermal layers of the skin but remained higher than uninjured levels.

RT-PCR analysis of mRNA isolated from the wound site confirmed the above findings by showing parallel increases in RHAMM expression (FIGS. 7A–B). The use of oligonucleotide primers that detected all RHAMM isoforms showed an increase in RHAMM mRNA at 12 h after injury and levels were sustained above background for a week after injury. RHAMM expression was maximal at 48 h after injury. RHAMM 4 was a minor fraction of total RHAMM assessed with RT-PCR and an increase in the level of this isoform was evident at 6 h after injury and declined towards baseline levels thereafter.

Injury to the skin was also accompanied by additional changes in extracellular matrix remodelling. HA content of control wounds detected by biotinylated aggrecan using an ELISA was increased by 8 h, and glucosaminidase activity indicating macrophage content was also increased by 24 h after injury (FIGS. 8 and 9A–D). The cell type responsible for the enhanced HA production was not ascertained but histochemical analysis indicated that accumulation occurred within the regenerating dermis and subdermis of the wound site (FIGS. 9A–D). HA levels returned to background levels at 36 h after injury. Such changes to skin HA levels were confirmed by enzyme assays.

Figure 13:
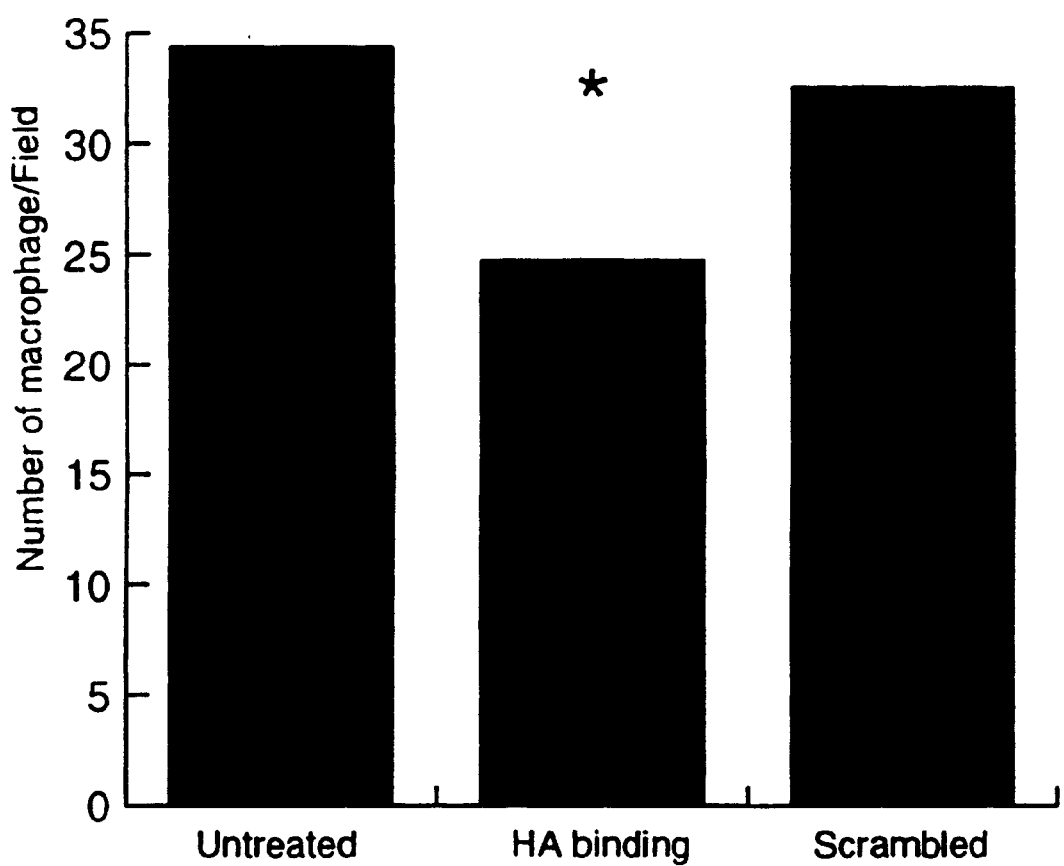
Figure 14:
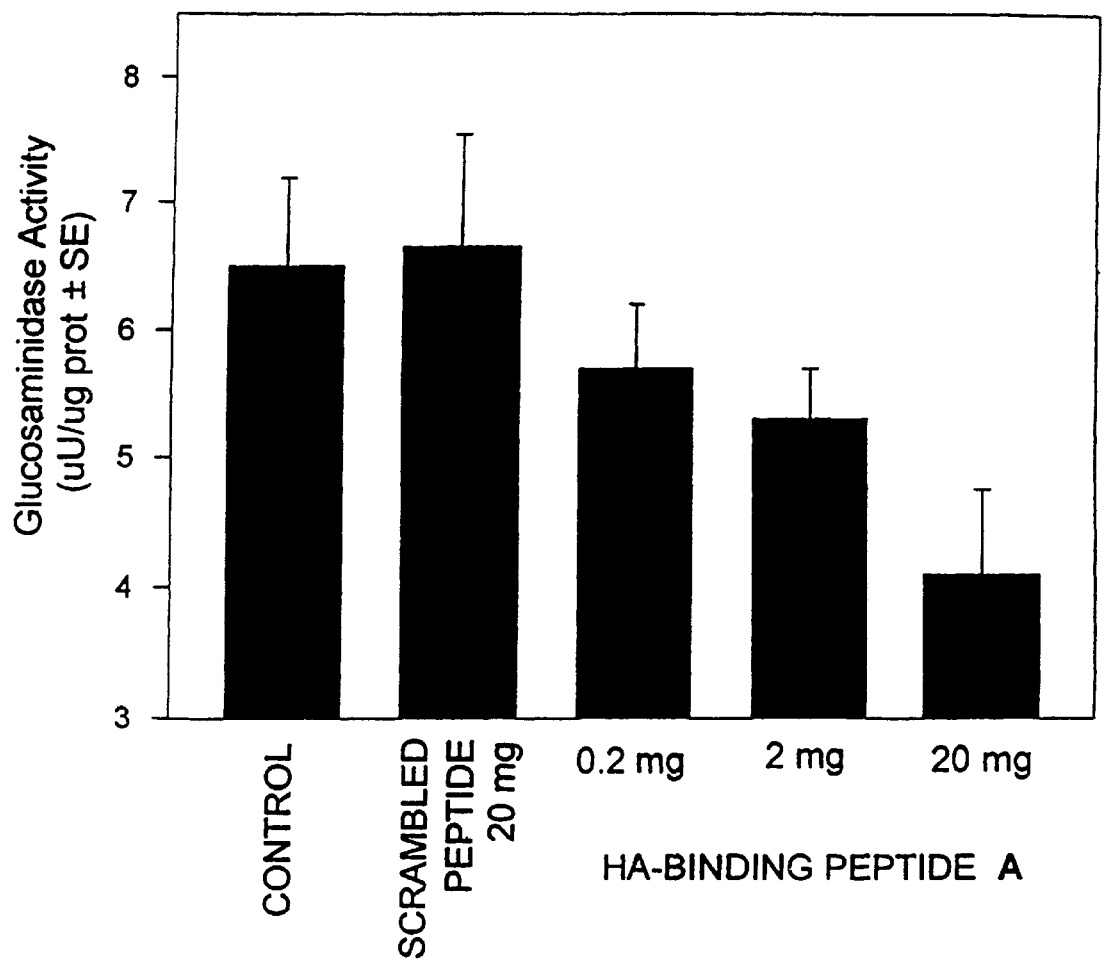

Collagen production as determined by histochemical and PT-PCR analyses was also found to be increased following skin injury. Increase in collagen type I production paralleled the infiltration of fibroblasts into the wound site. Level of collagen type I mRNA increased to a maximum at 3 to 4 days and declined towards basal levels over the subsequent 2 weeks (FIGS. 10A–B). The level of collagen type III which is predominantly produced by fibroblasts and white blood cells increased more rapidly (FIGS. 10C–D). Collagen type III mRNA level was notably increased by 6 h following injury, peaked at 24 h, and declined towards baseline values by 4 days (FIG. 10D). The timing of the acute increases in HA (FIG. 8) and collagen type III (FIG. 10D) coincided with the infiltration of leukocytes into the wound site and the resurfacing of the wound by the epidermal layer. Similarly, the timing of collagen type I elevation coincided with the infiltration of fibroblasts into the wound site (FIGS. 10B and 13).

Effects of HA-Binding Peptides on Wound Repair

Enhanced affinity HA binding peptides obtained from the phage display library were assessed for their effect on the course of wound repair. Administration of enhanced affinity HA binding peptide (shown in SEQ.ID.NO.:3) inhibited keratinocyte resurfacing of the wound (FIGS. 12 II & IV) and reduced the number of fibroblasts at the wound site (FIG. 17B). Leukocyte infiltration into the wound, as assessed by morphological examination, mac-3 and ED-1 staining and glucosaminidase measurement, was also reduced by enhanced affinity HA binding peptides relative to the scrambled peptide controls (FIG. 12(IV)). Leukocytes appeared to accumulate at the wound periphery but did not infiltrate into the wound site.

Figure 15:
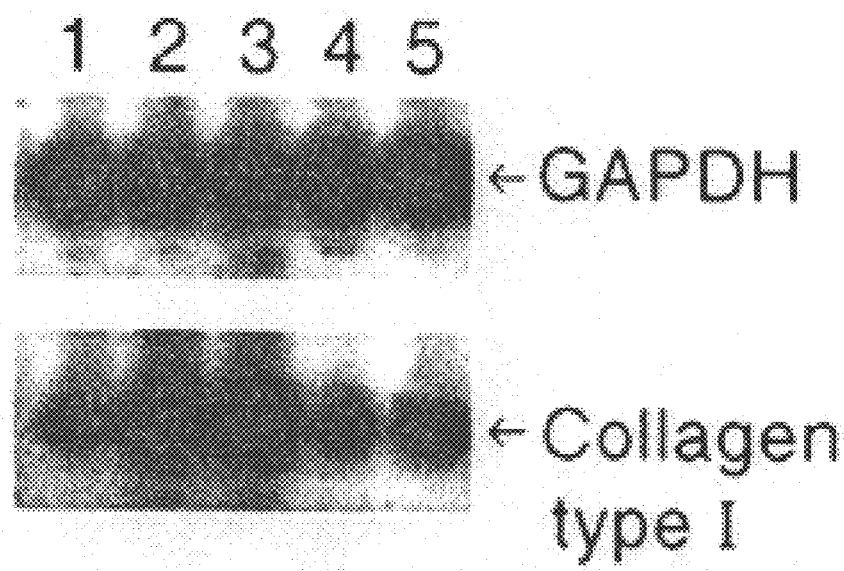

The effect of enhanced affinity HA binding peptides on HA accumulation and collagen production were also assessed. As shown in FIGS. 9A–D, treatment of wound sites with enhanced affinity HA binding peptide (shown in SEQ.ID.NO.:3) resulted in an increase in HA accumulation within the remodelling dermal layer at 24 h. Staining disappeared when tissue sections were pretreated with Streptomyces hyaluronidase indicating that the biotinylated aggrecan used to detect HA was specific for this glycosaminoglycan (FIGS. 9A–D). These results are consistent with the ELISA analysis (FIG. 8) of HA levels in injured skin that showed a peak accumulation of HA at 8 h and a reduction to background levels by 24–36 h following injury. Enhanced affinity HA binding peptides also reduced levels of collagen types I and III at 24 h as confirmed by mRNA determination by RT-PCR (FIGS. 15 and 16A–B).

Figure 4:
Figure 5:
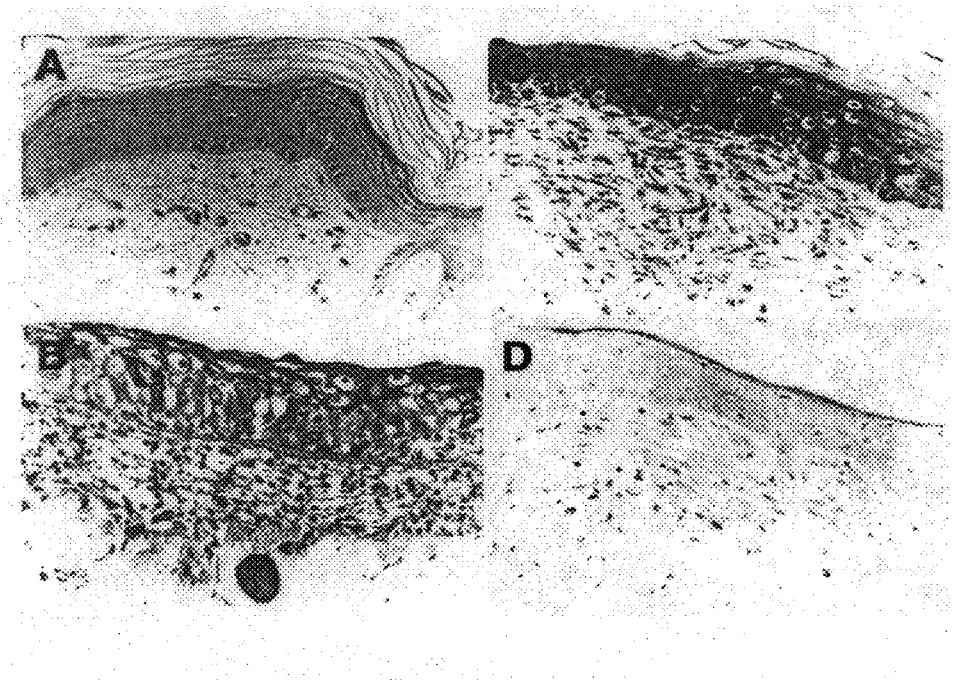
Figure 6:
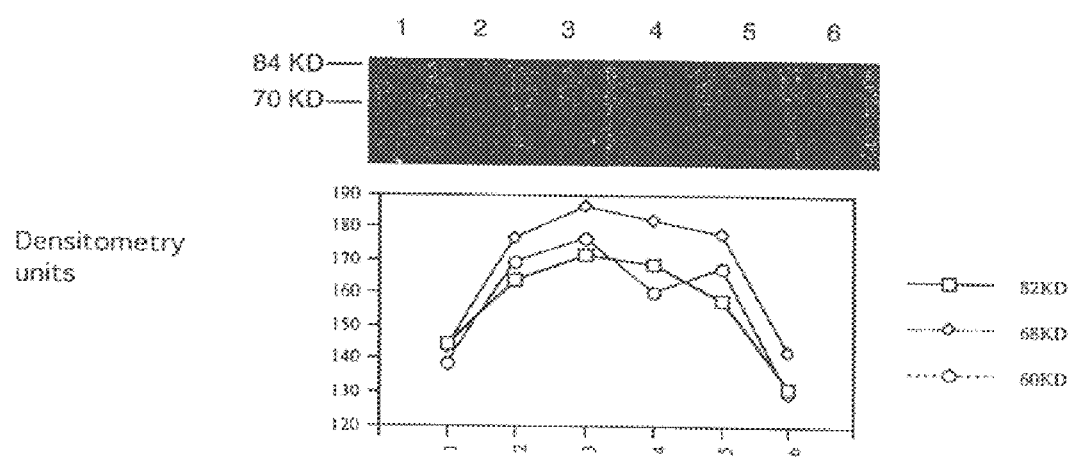
Figure 8:
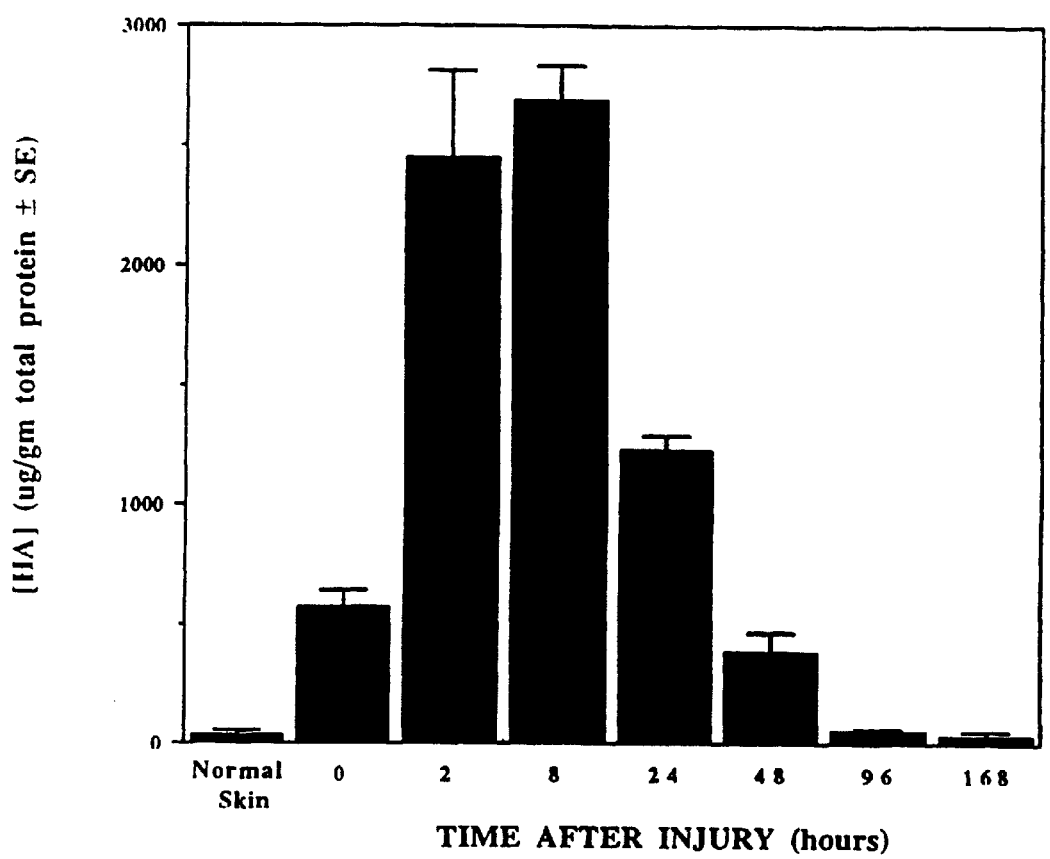
Figure 11:
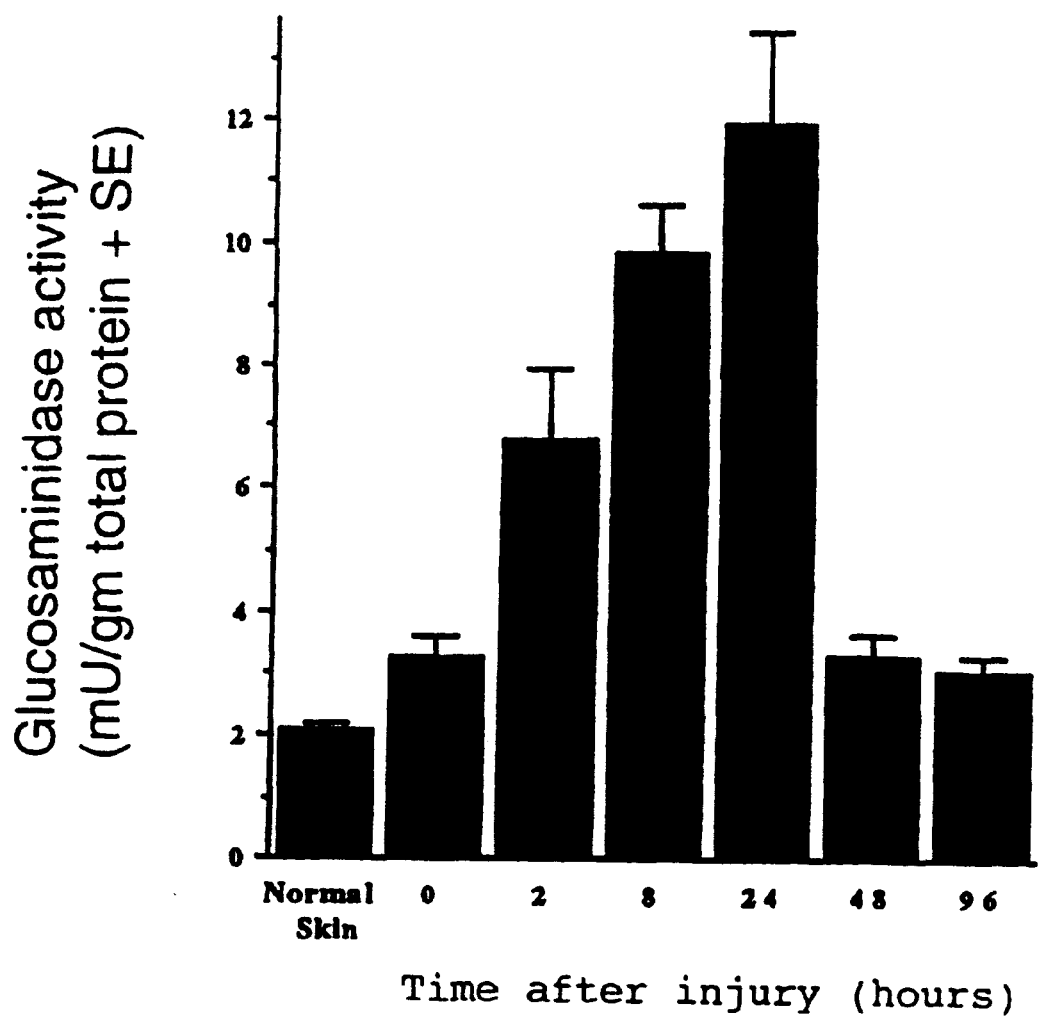
Figure 12:
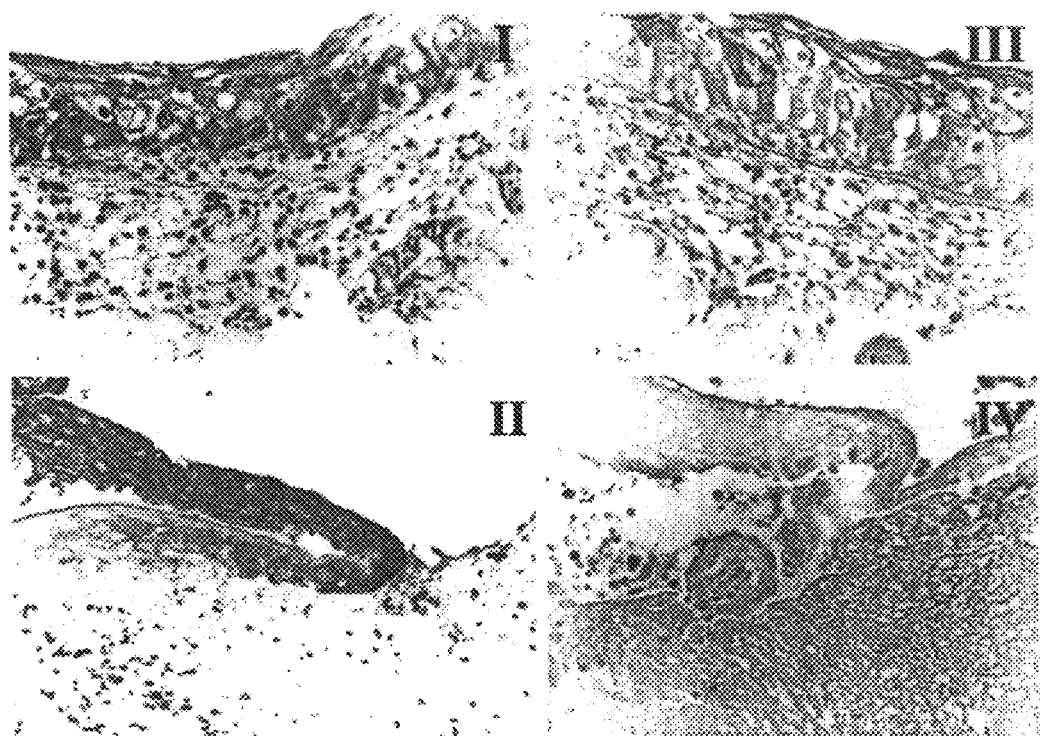

Treatment of wound sites with enhanced affinity HA binding peptides resulted in down-regulation of RHAMM and CD44 receptors as analyzed by RT-PCR (FIG. 4). Immunohistochemical analysis indicated that these receptors were depleted in keratinocytes, leucocytes and fibroblasts. The results indicate that RHAMM display was reduced per cell present within the wound and did not reflect an artifact associated with the reduced number of cells such as leucocytes and fibroblasts within the wound site. Similarly, addition of a monoclonal antibody specific for RHAMM (3T3-5 (Turley, E. A. et al., *J. Cell. Biol.* 112: 1041–1047, 1991)), previously shown to block cell motility (Turley, E. A. et al., *J. Cell. Biol.* 112: 1041–1047, 1991; Hall, C. L. et al., *Cell* 82: 19–28, 1995), inhibited re-epithelialization and leukocyte infiltration (FIG. 12 IV) to a similar extent to the enhanced affinity HA binding peptides (FIG. 12 II). These data confirm that RHAMM, in addition to CD44, is involved in cell migration and wound repair and that the effect of enhanced affinity HA binding peptides is mediated through RHAMM antagonism.

Figure 17:
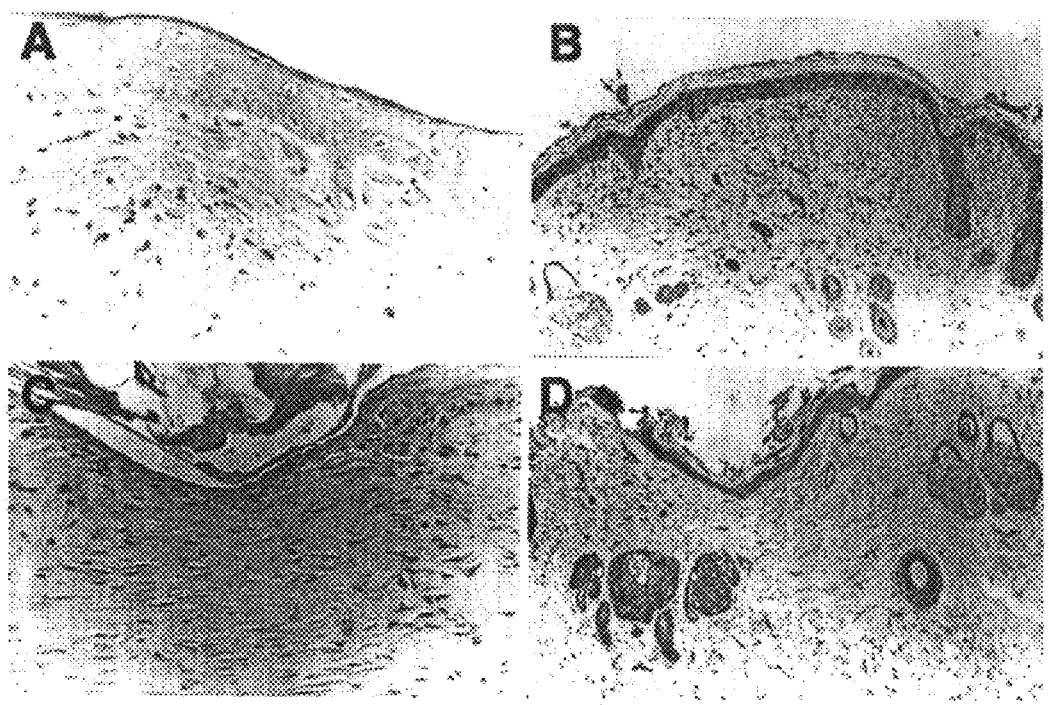
FIG. 17 shows photographs of paraffin sections of wound biopsies 2 weeks after injury which were stained with hematoxylin (A, B) or for RHAMM (C, D).

These changes in remodelling of the extracellular matrix coincided with a change in the morphology of the wound site at 2 weeks post injury (FIG. 17). The epidermal layer overlying the wound site was thicker in HA-binding peptide-treated skin as compared to control skin. In control skin, the injured site is contracted while fibroblasts and collagen fibrils were aligned parallel to each other as determined by trichrome staining (FIGS. 17A–B). In contrast, skin treated with HA-binding peptides did not show contraction and the skin resembles the surrounding uninjured skin. Tensometry analysis indicated that the skin strength of control versus treated wounds was not different and wound breaking was not observed.

Example 4
Mechanism of Action for HA-Binding Peptides in Tissue Fibrosis

Collagen Fibrillar Matrix (CFM) Assay

Tissue repair primarily consists of three overlapping phases consisting local inflammation, granulation tissue formation, and scar formation. The fibroproliferative response in wound repair is characterized by the concentric alignment of fibroblasts around the wound and production of collagen type I to form the major extracellular matrix or scar. Fibrotic wound repair is a pathology where excesssive formation of scar tissue is formed at the wound site as a result of excessive wound contraction and collagen deposition by fibroblasts.

In order to examine the ability of HA-binding peptides to reduce tissue fibrosis, a floating collagen fibrillar matrix (CFM) assay was established as a measure of fibroblast contraction using Vitrogen 100 (Collagen Corporation, Palo Alto, Calif.). Furthermore, the effects of 3 anti-RHAMM monoclonal antibodies (against exons 4, 5 and 9 of RHAMM protein), an anti-CD44 monoclonal antibody, as well as a RHAMM-motif peptide as described in PCT published application no. WO 93/21312, were also examined for elucidation of the underlying mechanism(s) of action. These monoclonal antibodies and RHAMM-motif peptide have been previously shown to inhibit HA binding to its receptors, RHAMM and CD44.

In the assay, CFM was formed in 24-well non-stick cultureware and were pre-equilibrated with 2 changes of alpha-modified Eagle's medium (alpha-MEM). The concentrations of HA-binding peptide studied were 1 ng/mL to 500 ug/mL. Each concentration of HA-binding peptide was resuspended in 10% fetal bovine serum (FBS) in alpha-MEM medium and 0.9 mL of such HA-binding peptide dilution was added to each well. Gels and media with or without HA-binding peptide were allowed to equilibrate overnight at 37° C. with 5% $CO_2$. On the following day, 100 uL of human foreskin fibroblasts were added to each CFM well in 10% FBS and alpha-MEM at a concentration of $0.1 \times 10^6$ cells/mL. Cells were evenly distributed by rotating the cultureware for 15 seconds. Final culture media composed of 1 ng/mL, 10 ng/mL, 100 ng/mL. 100 ug/mL or 500 ug/mL of HA-binding peptide in 1 mL alpha-MEM containing 10% FBS. Each experimental CFM with fibroblasts with or without HA-binding peptide were incubated at 37° C. with 5% $CO_2$. After plating the fibroblasts for 2 h, CFMs were detached from the bottoms of the wells. Photographs were taken at different times, up to 48 h. Areas of CFMs were measured by using NIH Image 1.6267.

CFM Results

Figure 18:
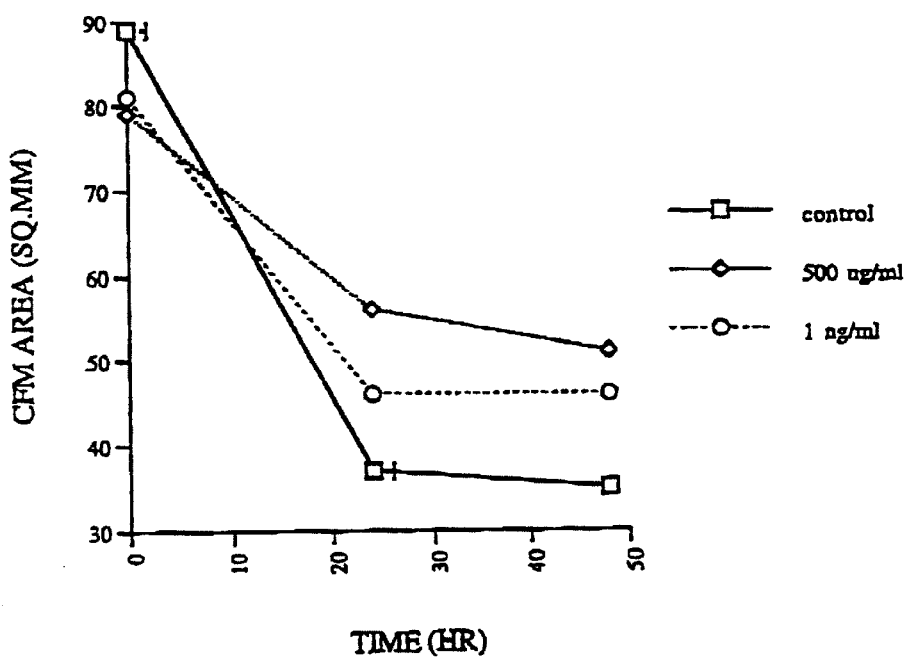
FIG. 18 shows a graph illustrating the inhibition of human foreskin fibroblasts contraction by 1 ng/mL and 500 mg/mL of HA-binding peptides as compared to the null effect of the negative control vehicle.
Figure 19:
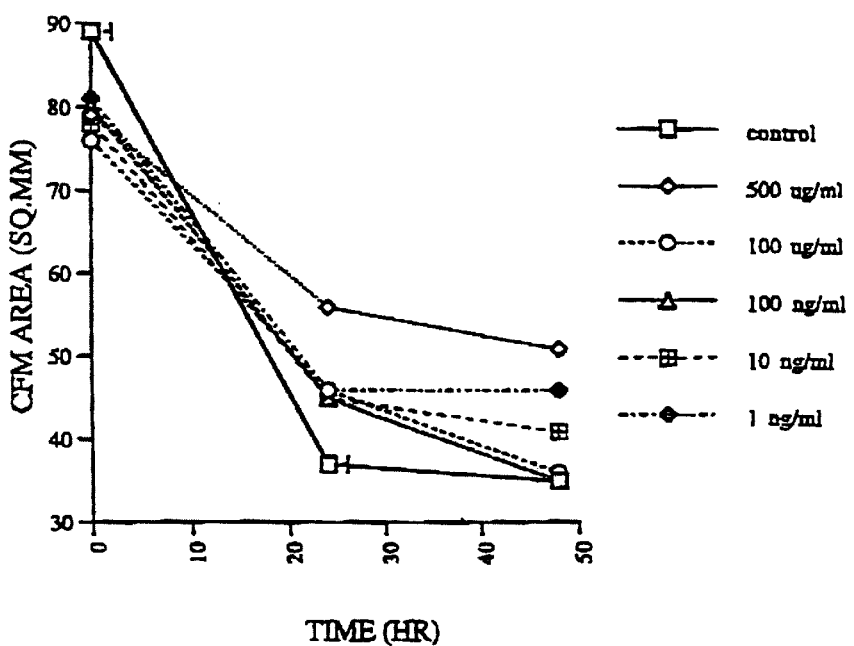
FIG. 19 shows a graph illustrating the inhibition of human foreskin fibroblasts contraction of HA-binding peptides in a dose-dependent manner as compared to the null effect of the negative control vehicle.

The current CFM assay showed a dose-dependent inhibition of human foreskin fibroblasts contraction by enhanced affinity HA-binding peptides of the present invention as compared to control (FIGS. 18 and 19) thereby indicating its efficacy in reducing wound contraction in fibrotic wound healing. The effective concentration range of said HA-binding peptides is 1 ng/mL to 500 ug/mL.

Figure 20:
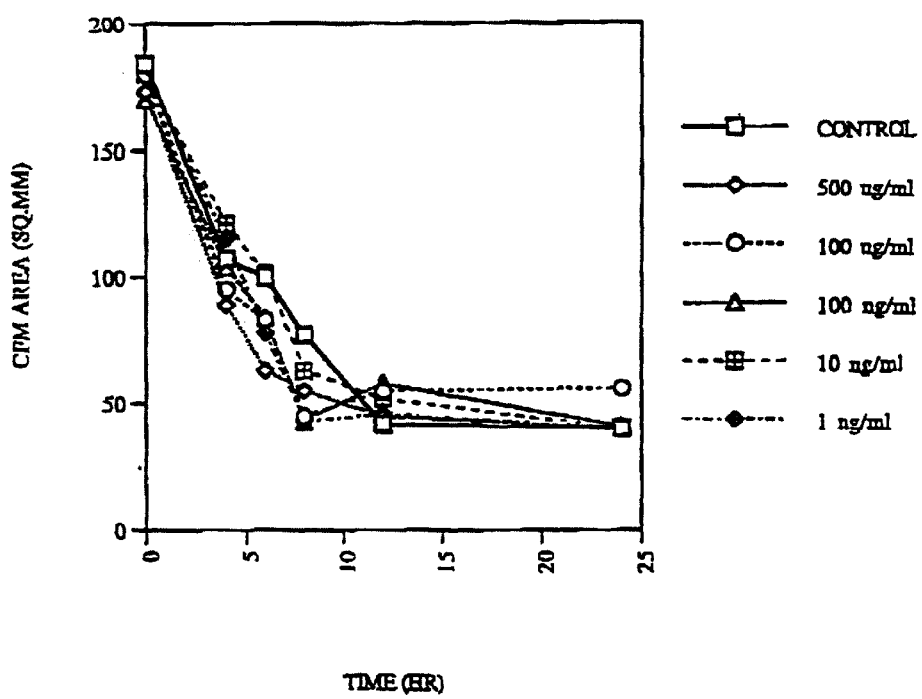
FIG. 20 shows a graph illustrating the null effect of RHAMM-motif peptide (1 ng/mL and 500 mg/mL) on human foreskin fibroblasts contraction.
Figure 21:
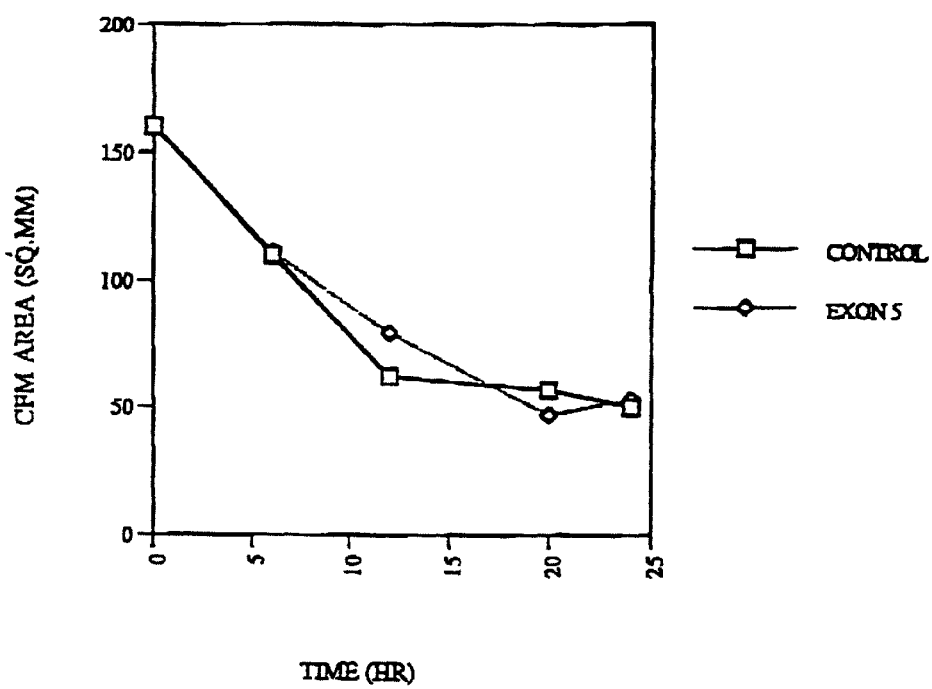
FIG. 21 shows a graph illustrating the null effect of anti-RHAMM (exon 5) antibodies on human foreskin fibroblasts contraction.
Figure 22:
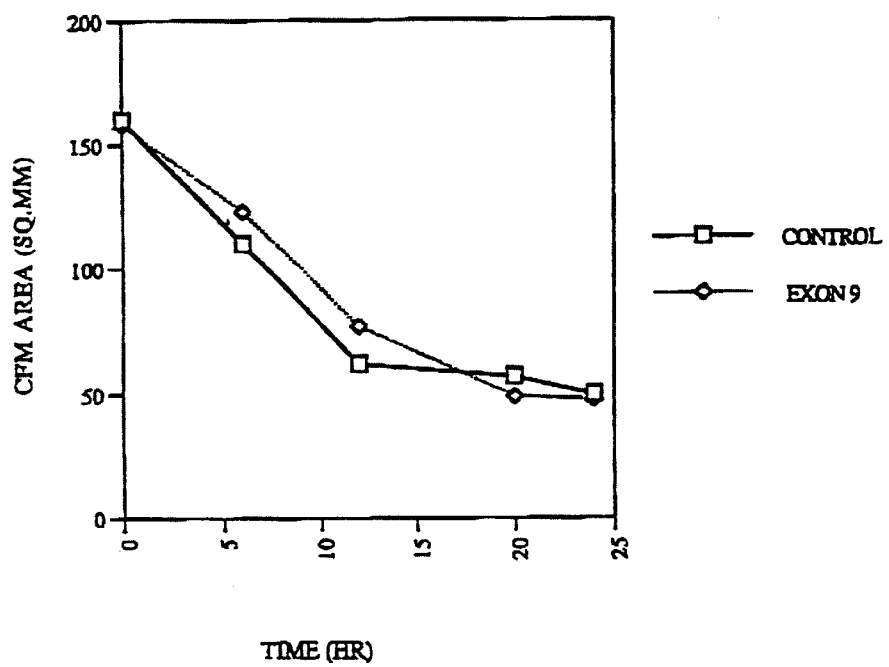
FIG. 22 shows a graph illustrating the null effect of anti-RHAMM (exon 9) antibodies on human foreskin fibroblasts contraction.

In order to further distinguish the HA-binding peptides of the present invention from the RHAMM-motif peptides as described in PCT published application no. WO 93/21312, the present experimentation has shown that the latter RHAMM-motif peptides, over the same concentration range, are not effective in inhibiting human foreskin fibroblasts contraction (FIG. 20). Since the RHAMM-motif peptides resemble the receptor domains in RHAMM responsible for HA binding and are known to inhibit HA binding to RHAMM, the failure of RHAMM-motif peptides to reduce tissue contraction indicates that the enhanced affinity HA-binding peptides of the present invention do not inhibit tissue contraction by interfering with HA binding to RHAMM. This observation is further supported by the fact that addition of 2 anti-RHAMM (anti-exon-5 and anti-exon-9) monoclonal antibodies did not affect human fibroblasts contraction as determined by the CFM assay (FIGS. 21 and 22).

Figure 23:
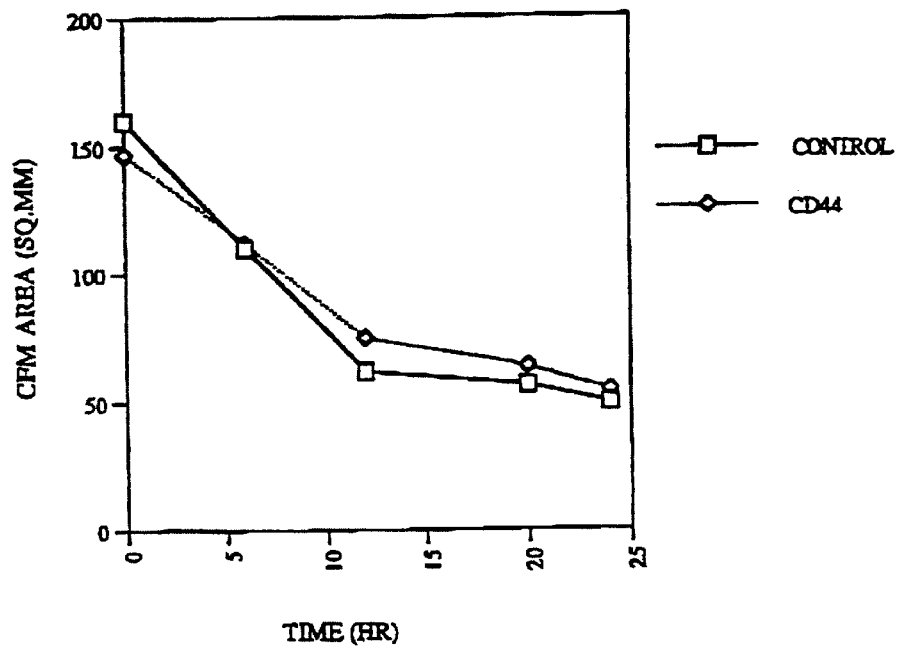
FIG. 23 shows a graph illustrating the null effect of anti-CD44 antibodies on human foreskin fibroblasts contraction.

Furthermore, addition of an anti-CD44 monoclonal antibody also did not inhibit fibroblasts contraction in the CFM assay suggesting that the inhibitory effects of the HA-binding peptides of the present invention are not mediated by interference of HA binding to CD44 (FIG. 23).

Having illustrated and described the principles of the invention in a preferred embodiment, it should be appreciated by those skilled in the art that invention can be modified in arrangement and detail without departure from such principles. I claim all modifications coming within the scope of the following claims.

TABLE I

DNA Sequences for An Enhanced Affinity
HA-Binding Peptides

SEQ ID NO. 5
For expression in *Escherichia coli*
A C C A T G A C C C G T C C G C A C T T C C A C A
A A C G T C A G C T G G T T C T G T C T SEQ ID NO.6
For expression in *Streptomyces lividans*
A C S A T G A C S C G S C C S C A C T T C C A C A
A G C G S C A G C T S G T S C T S W S S
wherein S is C or G and W is A or T.

SEQ ID NO. 7
For expression in *Escherichia coli*
T C T A C C A T G A T G T C T C G T T C T C A C A
A A A C C C G T T C T C A C C A C T G T SEQ ID NO. 8
For expression in *Streptomyces lividans*
W S S A C S A T G A T G W S S C G S W S S C A C A
A G A C S C G S W S S C A C C A C T G C
wherein S is C or G and W is A or T.

SEQ.ID.NO. 9
For expression in *Escherichia coli*
TCT ACC ATG ATG TCT CGT TCT CAC AAA ACC CGT TCT
CAC CAC
wherein S is C or G and W is A or T.

SEQ.ID.NO. 10
For expression in *Streptomyces lividans*
WSS ACS ATG ATG WSS CGS WSS CAC AAG ACS CGS WSS
CAC CAC
wherein S is C or G and W is A or T.

SEQ.ID.NO.: 11
For expression in *Escherichia coli*

TABLE I-continued

DNA Sequences for An Enhanced Affinity HA-Binding Peptides

TCT ACC ATG ATG TCT CGT TCT CAC AAA ACC CGT TCT CAC CAC GTG
wherein S is C or G and W is A or T.

SEQ.ID.NO.: 12
For expression in *Streptomyces lividans*
WSS ACS ATG ATG WSS CGS WSS CAC AAG ACS CGS WSS CAC CAC GTC
wherein S is C or G and W is A or T.

TABLE II

Effect of Peptide on Cell Locomotion

| A: Cell Type | | Rate of Locomotion | |
|---|---|---|---|
| | | Scrambled Peptide (um/h) | HA-Binding Peptide (STMMSRSHKTRSHH) (47) (um/h) |
| a) | Random locomotion* | | |
| | Fibroblast (ras transformed) | 34.04 ± 3.57 | 10.83 ± 1.07 |
| | Alveolar macrophages | 8.67 ± 1.13 | 3.24 ± 0.53 |
| b) | Chemotaxis⁺ | | |
| | Human neutrophils (to IL-8) | 0.287 ± 0.013 | 0.088 ± 0.009 |
| | Rat alveolar macrophages (to C5a) | 0.768 ± 0.063 | 0.425 ± 0.028 |

TABLE II-continued

Effect of Peptide on Cell Locomotion

| A: Cell Type | Rate of Locomotion | |
|---|---|---|
| | Scrambled Peptide (um/h) | HA-Binding Peptide (STMMSRSHKTRSHH) (47) (um/h) |
| S1 macrophage cell line (to C5a) | 0.676 ± 0.046 | 0.238 ± 0.014 | n = 100 cells for random locomotion and n = 3 replicates ± SD of mean for chemotaxis assays.
*Random locomotion was assayed by quantifying nuclear displacement using image analysis.
⁺Chemotaxis was measured in a standard Boyden chamber assay using MTT blue to detect live cells. Reselts are means ± SEM.

TABLE III

Effect of HA-Binding Peptides on Cell Proliferation in Response to Serum and Apoptosis

| Treatment* | Number of Cells ($\times 10^6$) | % Hoechst Positive Nuclei |
|---|---|---|
| Control | 2.5 ± 0.2 | 2.0 ± 0.8 |
| Positive Control (PD98059, MEK inhibitor) | 0.5 ± 0.1 | 40 ± 2.5 |
| HA-Binding Peptide (STMMSRSHKTRSHH) | 2.4 ± 0.2 | 4.9 ± 0.9 |

*Cells were treated with 100 ug/mL peptide or a MEK inhibitor PD98059 (50 ug/mL). Cell number was determined with hemocytometer counts and apoptosis by the number of Hoechst dye positive nuclei.

---

I claim:

1. A hyaluronic acid (HA)-binding peptide consisting of:
(a) a sequence of the formula I:

$$X_1-X_2-X_1-X_3-X_4-X_3-X_4-X_3-X_3-X_3-X_5-X_6-X_6-X_6-X_1$$

wherein each $X_1$ is independently selected from a hydroxy amino acid residue;

each $X_2$ is independently selected from a sulfur containing amino acid residue;

each $X_3$ is independently selected from a basic amino acid residue;

each $X_4$ is independently selected from an imino or aromatic amino acid residue;

each $X_5$ is independently selected from a dicarboxylic acid amino acid residue; and each $X_6$ is independently selected from an aliphatic amino acid residue;

(b) a sequence of the formula II:

$$Y_1\text{-}Y_1\text{-}Y_2\text{-}Y_2\text{-}Y_1\text{-}Y_3\text{-}Y_1\text{-}Y_3\text{-}Y_3\text{-}Y_1\text{-}Y_3\text{-}Y_1\text{-}Y_2\text{-}Y_3\text{-}Y_3$$

wherein each $Y_1$ is independently selected from a hydroxy amino acid residue;

each $Y_2$ is independently selected from a sulfur containing amino acid residue; and each $Y_3$ is independently selected from a basic amino acid residue; or (c) a sequence of the formula III:

$$Z_1\text{-}Z_1\text{-}Z_2\text{-}Z_2\text{-}Z_1\text{-}Z_3\text{-}Z_1\text{-}Z_3\text{-}Z_3\text{-}Z_1\text{-}Z_3\text{-}Z_1\text{-}Z_3\text{-}Z_3$$

wherein each $Z_1$ is independently selected from a hydroxy amino acid residue;

each $Z_2$ is independently selected from a sulfur containing amino acid residue; and each $Z_3$ is independently selected from a basic amino acid residue.

2. A HA-binding peptide consisting of a sequence of the formula I as defined in claim 1 wherein each $X_1$ is independently selected from threonine or serine;

each $X_2$ is independently selected from methionine or cysteine;

each $X_3$ is independently selected from arginine, lysine or histidine;

each $X_4$ is independently selected from proline, phenylalanine or tryptophan;

each $X_5$ is independently selected from asparagine or glutamine; and each $X_6$ is independently selected from leucine, isoleucine, valine or alanine.

3. A peptide according to claim 2 consisting of the amino acid sequence TMTRPHFHKRQLVLS as shown in SEQ.ID.NO.:1.

4. A peptide according to claim 3 wherein the amino acids in the peptide are the levorotatory (L) form.

5. A HA-binding peptide consisting of a sequence of the Formula II as defined in claim 1, wherein each $Y_1$ is independently selected from serine or threonine;

each $Y_2$ is independently selected from methionine or cysteine; and each $Y_3$ is independently selected from arginine, lysine or histidine.

6. A peptide according to claim 5 consisting of the amino acid sequence STMMSRSHKTRSCHH as shown in SEQ.ID.NO.:2.

7. A peptide according to claim 6 wherein the amino acids in the peptide are the levorotatory (L) form.

8. A HA-binding peptide consisting of a sequence of the formula III as defined in claim 1, wherein each $Z_1$ is independently selected from serine or threonine;

each $Z_2$ is independently selected from methionine or cysteine; and each $Z_3$ is independently selected from arginine, lysine or histidine.

9. A peptide according to claim 8 consisting of the amino acid sequence STMMSRSHKTRSHH as shown in SEQ.ID.NO.:3.

10. A peptide according to claim 9 wherein the amino acids in the peptide are the levorotatory (L) form.

11. A peptide according to claim 8 consisting of the amino acid sequence STMMSRSHKTRSHHV as shown in SEQ.ID.NO.4.

12. A peptide according to claim 11 wherein the amino acids in the peptide are the levorotatory (L) form.

* * * * *